United States Patent [19]

Sharp et al.

[11] Patent Number: 4,663,539
[45] Date of Patent: May 5, 1987

[54] LOCAL POWER SWITCHING CONTROL SUBSYSTEM

[75] Inventors: Larry D. Sharp, San Juan Capistrano; Alan T. Theis, Mission Viejo, both of Calif.

[73] Assignee: Burroughs Corporation, Detroit, Mich.

[21] Appl. No.: 676,150

[22] Filed: Nov. 29, 1984

[51] Int. Cl.⁴ .............................................. H02J 3/00
[52] U.S. Cl. ....................................... 307/38; 307/64; 307/66; 307/35; 361/90; 361/91; 364/492; 364/493; 364/200
[58] Field of Search ...................... 307/11, 18, 29, 30, 307/34, 35, 36, 37, 38, 39, 40, 41, 42, 43, 44, 46, 48, 64, 66, 69, 71, 75, 77, 80, 81, 85, 87; 361/88, 89, 90, 91, 92, 93, 412, 413, 415; 364/492, 493, 495

[56] References Cited

U.S. PATENT DOCUMENTS

| | | | |
|---|---|---|---|
| 3,573,554 | 4/1971 | Theobald | 361/90 |
| 3,997,879 | 12/1976 | Markley et al. | 364/184 X |
| 4,100,426 | 7/1978 | Baranowski et al. | 307/41 |
| 4,136,393 | 1/1979 | Fox | 307/41 X |
| 4,175,238 | 11/1979 | Breimesser et al. | 307/40 |
| 4,204,249 | 5/1980 | Dye et al. | 307/64 X |
| 4,321,477 | 3/1982 | Bartlett | 307/41 X |
| 4,352,992 | 10/1982 | Buennagel et al. | 307/40 |
| 4,451,742 | 5/1984 | Aswell | 307/66 |
| 4,510,398 | 4/1985 | Culp et al. | 307/41 X |
| 4,527,071 | 7/1985 | Ausiello | 307/81 |
| 4,528,458 | 7/1985 | Nelson et al. | 307/44 X |
| 4,531,240 | 7/1985 | Yokomizo | 307/66 X |
| 4,538,073 | 8/1985 | Freige et al. | 307/33 |
| 4,539,487 | 9/1985 | Ishii | 307/64 X |

Primary Examiner—William M. Shoop, Jr.
Assistant Examiner—Shik Luen Paul Ip
Attorney, Agent, or Firm—Alfred W. Kozak; Nathan Cass; Kevin R. Peterson

[57] ABSTRACT

Each digital module in a network is provided with a local power switching control subsystem wherein the local module uses a local power switching control logic card which controls main power and subordinate power units in a predetermined sequence. Power up-/down conditions or incremental/decremental voltage conditions can be effected by a local operator or by an instruction from a remote master logic unit. The power subsystem can sense failure conditions and communicate this information to the remote master unit or to a local operator.

14 Claims, 18 Drawing Figures

SYSTEM--FUNCTIONAL DIAGRAM.

FIG.1. SYSTEM--FUNCTIONAL DIAGRAM.

FIG.2. PROCESSOR CABINET.

FIG. 3. DEPENDENTLY-POWERED I/O CABINET.

FIG. 4.  INDEPENDENTLY-POWERED CABINETS.

FIG.5. POWER CONTROL NETWORK.

FIG. 8. MASTER LOGIC BLOCK DIAGRAM.

FIG. 9. PERIPHERAL SLAVE BLOCK DIAGRAM.

FIG. 10.
POWER CONTROL NETWORK PROTOCOL.
| | FROM MASTER TO SLAVE | FROM SLAVE TO MASTER |
|---|---|---|
| | msb | |
| 1. | 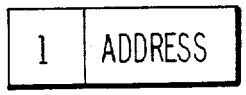 | |
| 2. | |  |
| 3. |  | |
| 4. | |  |
| 5. | 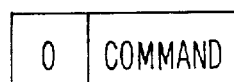 | |
| 6. | | 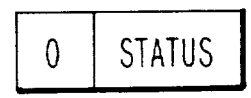 |
NETWORK BYTE FORMAT
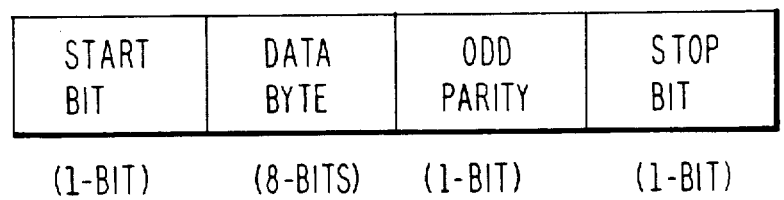
(1-BIT)　　(8-BITS)　　(1-BIT)　　(1-BIT)

POWER NETWORK FLOW FOR THE MASTER.

NOTE:
MASTER ALSO CHECKS FOR VERTICAL PARITY AND FRAMING ERRORS ON SLAVE RESPONSE TRANSMISSIONS.

FIG.12. SLAVE PROTOCOL.

NOTE:

THE SLAVE ALSO CHECKS FOR VERTICAL PARITY AND FRAMING ERRORS ON BYTES RECEIVED FROM THE MASTER.

SLAVE PORTS A & B -- OUTPUT SIGNALS.

SLAVE PORT A or B (SEE FIG. 7.)

*NOTES:

(1) POWER ON/OFF SIGNAL -- (0=ON) & (1=OFF).

(2) SIGNALS REMAINS ACTIVE AS LONG AS THE SPECIFIC CONDITION IS REQUIRED.

(3) RESET SIGNAL IS A PULSE LASTING AT LEAST 10 MILLISECONDS.

FIG. 14. SLAVE PORTS A & B -- INPUT SIGNALS.

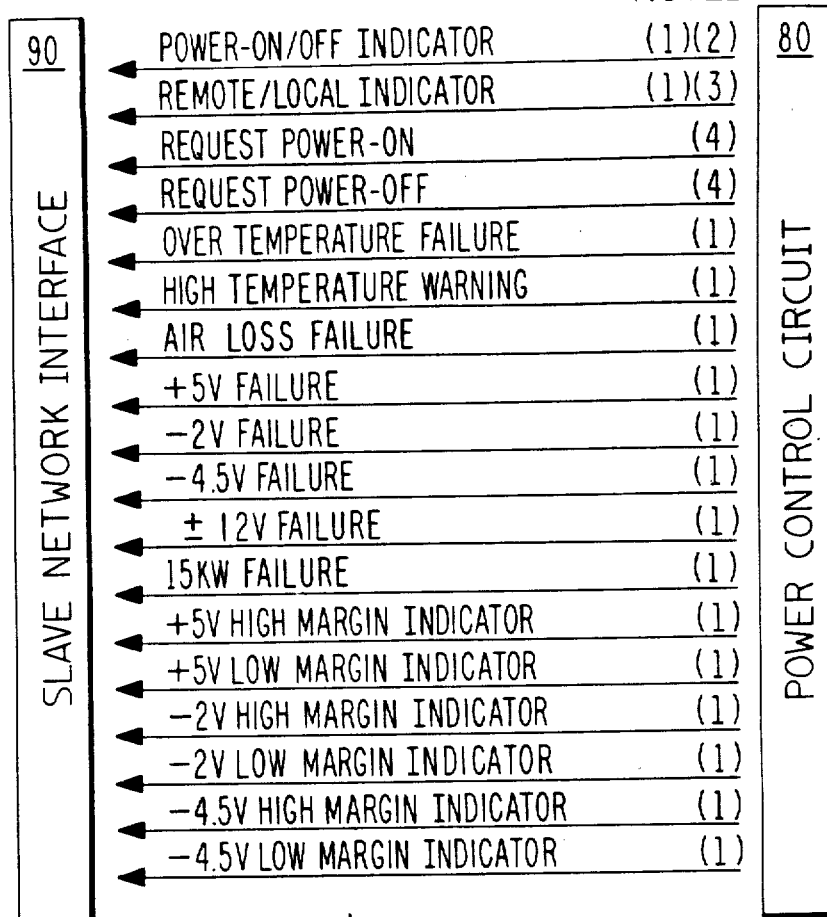

| 90 | | NOTES |  80 |
|---|---|---|---|
| | POWER-ON/OFF INDICATOR | (1)(2) | |
| | REMOTE/LOCAL INDICATOR | (1)(3) | |
| | REQUEST POWER-ON | (4) | |
| | REQUEST POWER-OFF | (4) | |
| | OVER TEMPERATURE FAILURE | (1) | |
| | HIGH TEMPERATURE WARNING | (1) | |
| | AIR LOSS FAILURE | (1) | |
| | +5V FAILURE | (1) | |
| | −2V FAILURE | (1) | |
| | −4.5V FAILURE | (1) | |
| | ±12V FAILURE | (1) | |
| | 15KW FAILURE | (1) | |
| | +5V HIGH MARGIN INDICATOR | (1) | |
| | +5V LOW MARGIN INDICATOR | (1) | |
| | −2V HIGH MARGIN INDICATOR | (1) | |
| | −2V LOW MARGIN INDICATOR | (1) | |
| | −4.5V HIGH MARGIN INDICATOR | (1) | |
| | −4.5V LOW MARGIN INDICATOR | (1) | |

(90 = SLAVE NETWORK INTERFACE; 80 = POWER CONTROL CIRCUIT)

*NOTES
(1) SIGNAL REMAINS ACTIVE AS LONG AS THE CONDITION CONTINUES.
(2) POWER ON/OFF SIGNAL -- (0=ON) & (1=OFF).
(3) REMOTE/LOCAL SIGNAL -- (0=REMOTE) & (1=LOCAL).
(4) POWER ON REQUEST AND POWER OFF REQUEST SIGNALS ARE FOR PROCESSOR CABINETS ONLY. THEY ARE A PULSE OF ONE MILLISECOND MINIMUM.

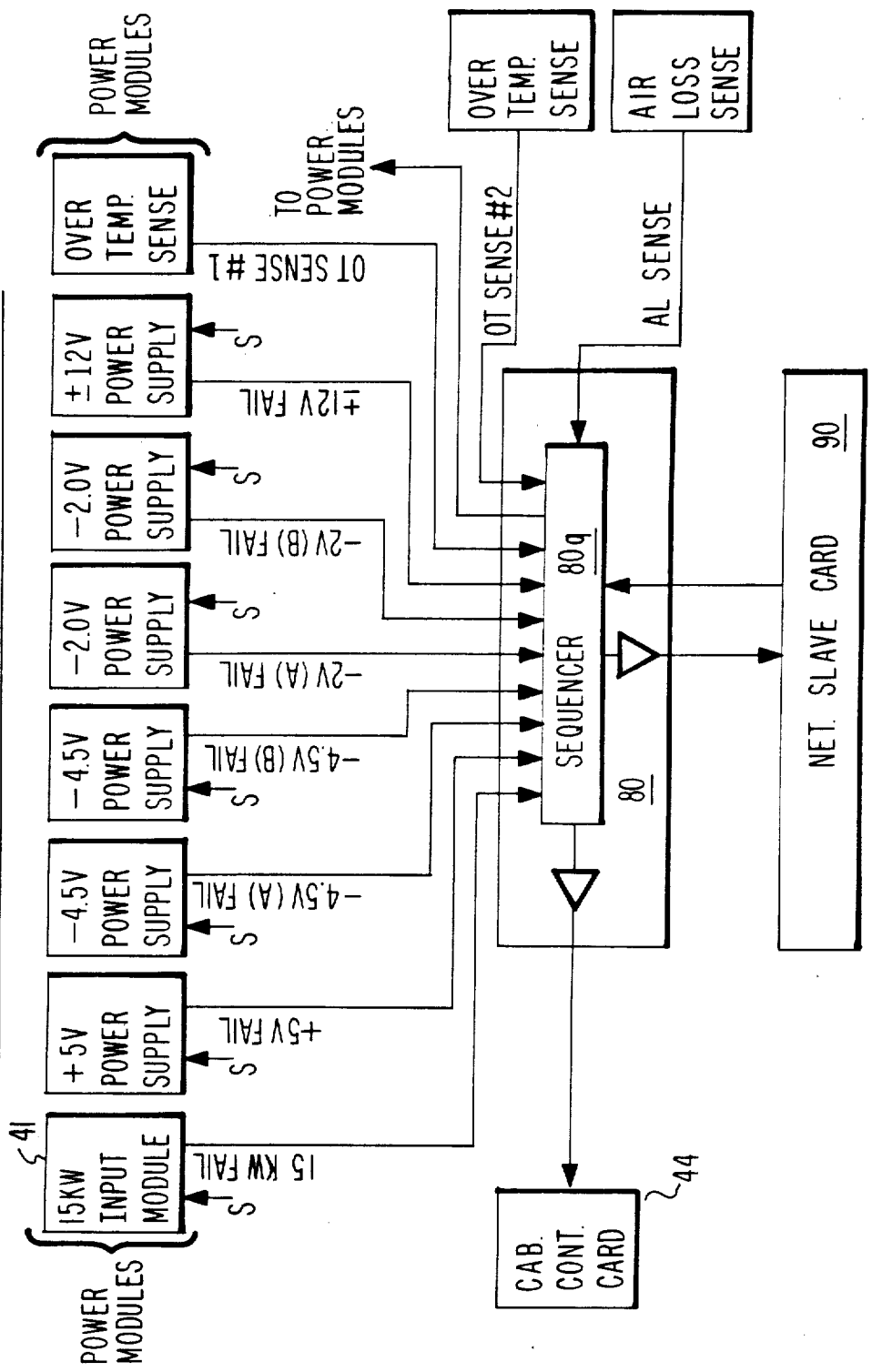
FIG.15. BLOCK DIAGRAM OF FAILURE DETECTION AND CONTROL.

LOCAL POWER SWITCHING CONTROL SUBSYSTEM

FIELD OF THE INVENTION

This disclosure involves the field of computer system networks and is specifically directed to handling the problems of power control in each of the various units involved in the system network, by the use of a master-slave logic system which controls each local power switching logic unit.

CROSS REFERENCES TO RELATED INVENTIONS

This disclosure is related to an application entitled "Power Control Network for Multiple Digital Modules", filed Oct. 18, 1984, as U.S. Pat. Ser. No. 662,477, by inventors Bruce E. Whittaker, James H. Jeppesen, III, and Larry D. Sharp.

BACKGROUND OF THE INVENTION

In the present day advance of computer and communications network technology, it is now possible that many types of units are interconnected both by direct bus connection and by remote telephone lines. These networks may involve a variety of processors, a variety of input/output systems located in separate cabinets, plus other cabinetry in addition to large portions of memory cabinetry.

In such a separate and complex network, one major problem often arises as to the conditions of the supply power at each of the individual units in order that this system may operate intercooperatively and effectively.

For example, it is never known what the status or power condition of each of the interconnected units may be in relationship to the units which are powered up and operating.

Many times certain areas of the network may not be desired for use and in order to save power and energy, it is desired that these units be turned off for certain periods of time when not in use. Likewise, other units of this system may be desired for use and will need to be controlled or checked to make sure that the power conditions in these units are properly up.

Thus, in order to provide control and flexibility in a system and to make sure that all those units that are needed are powered up and operable, and those units which are not needed can be turned off to save energy and unnecessary use, it is important to system operators that some means be devised for knowing the power status of each and every unit in the system and also for being able to "centrally control", that is to say, to power up or to power down, each and every unit in the system as required.

To this end, the problems have been handled in this arrangement only catch as catch can, with the hope that each unit is powered up properly and each unit is sufficiently powered up to operate properly. Generally there has been no flexibility as to be able to shut down certain unused units when they are not needed also.

The presently devised power control network and local power switching system overcomes the major inadequacies involved in a large computer system network by providing a centralized power control logic system whereby the each and every one of the modules or cabinet units in this system may be communicated to, in order to find out their power status; and further commands may be transmitted to each addressed element in the system in order to power-up or to power-down the unit thus to provide the utmost flexibility and also provide the utmost in energy conservation permissible under the circumstances.

SUMMARY OF THE INVENTION

It has long been a problem in a complex system network which involves a multitude of independent processors, independent I/O systems, and independent memory systems to regulate the "on-off-ness" of power and the power status of each of the units in the system when all the units are able to communicate with each other.

The present system provides a central master power control logic unit which can communicate with a slave power control logic unit which is located in each individual system cabinet of the system. The central master power control logic unit can poll, and selectively address each and every unit in the system in order to control the condition of its power as to being on or off, or to select marginal voltage conditions, or to find out the power status of that particular unit.

Thus, one central location can operate to control and monitor the power conditions of each unit in the entire system so that no unit is inadvertently off-line or shut down or depowered without the knowledge of the central master power control logic unit.

The particular inventive focus in this disclosure involves a power switching control subsystem which is situated in each power cabinet and operates to control the on/off condition of the main power source and to sequence a series of subordinate power sources on/off depending on local operator switches or commands from the local slave logic unit. The power subsystem can make incremental voltage adjustments and also sense failure conditions arising in associated power modules. It can then take action to power down the system when necessary.

BRIEF DESCRIPTION OF THE DRAWINGS

FIG. 10 is a schematic diagram showing the protocol used for communication between master and slave units and additionally the byte format used.

FIG. 14 is an illustration showing the input signals from the power control circuit to the slave logic unit.

FIG. 15 shows a block diagram illustrating the circuitry for failure detection and power control.

General Overview:

This subsystem relates to a computer network and system which interconnects the following type of cabinets:

(a) processor cabinets;
(b) dependently-powered I/O cabinets;
(c) independently-powered I/O cabinets;
(d) independently-powered memory cabinets.

A "dependently-powered" cabinet is a cabinet which derives its AC power and its high voltage input DC power from another cabinet (other than itself)—in this case the other cabinet is called the "processor cabinet". Thus, the "dependently-powered" cabinet must be physically attached to the source cabinet.

An "independently-powered" cabinet is a cabinet which has its own AC power Source. It may, therefore, be considered as a "free-standing" unit.

Figure 1:
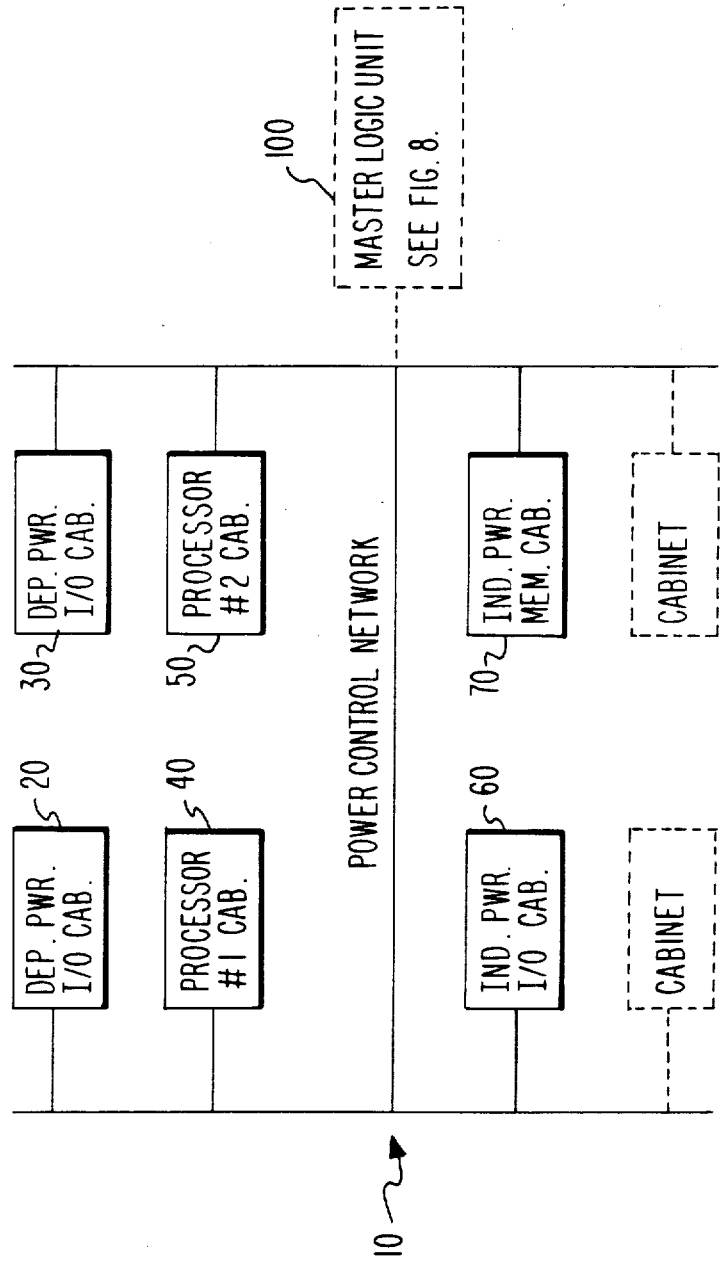
FIG. 1 illustrates a network of cabinets which house processors, I/O systems and memories whereby a power control network is connected to command and control the power conditions within each and every one of the connected cabinets.

FIG. 1 indicates a block diagram of the network power control subsystem 10. Shown therein are a dependent power I/O cabinet 20 and 30, in addition to two processor cabinets 40 and 50. Additionally connected to the power control network are the independent power I/O cabinets 60 and 70.

Figure 2:
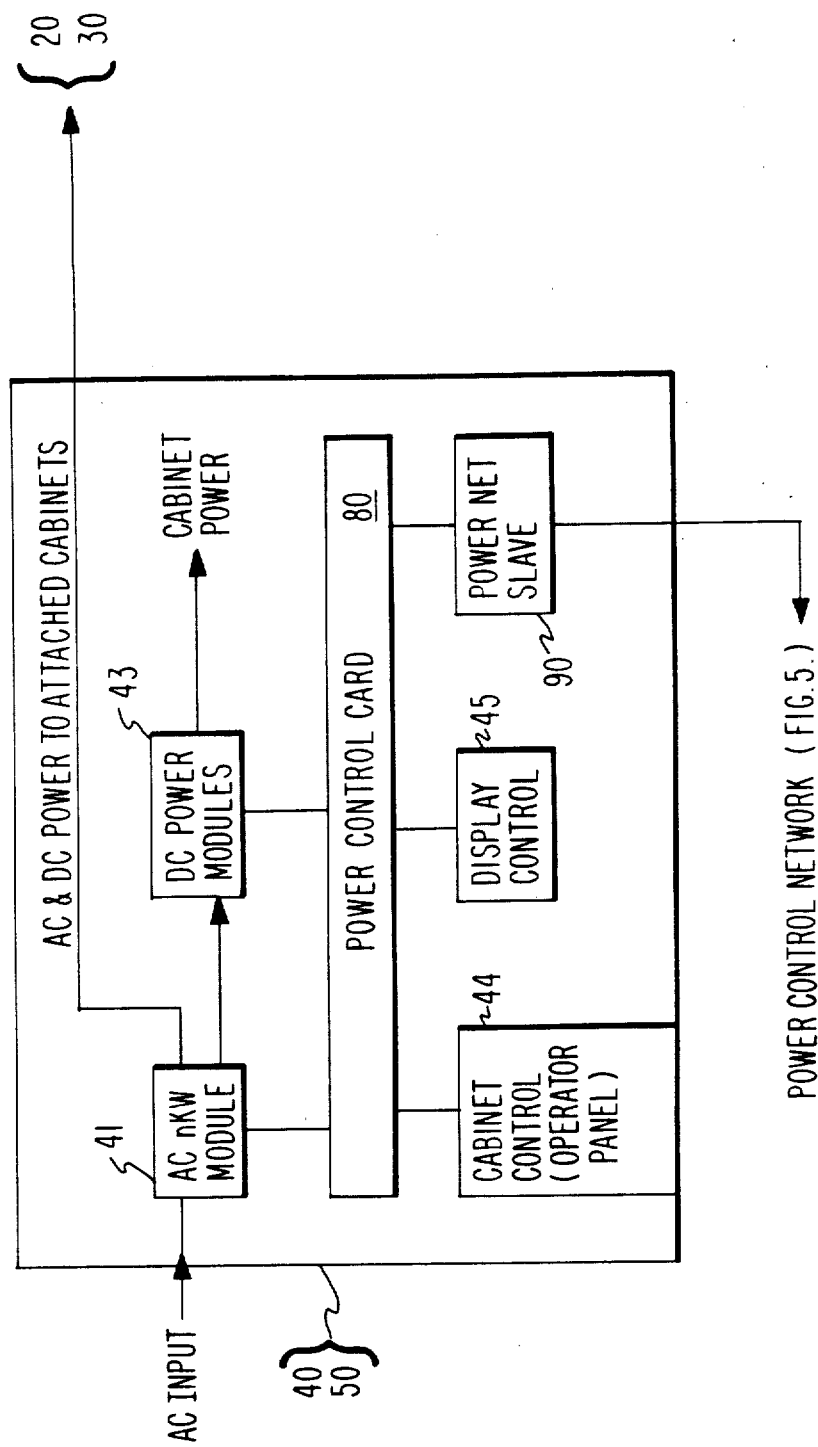
FIG. 2 is a block diagram of a typical processor type cabinet and its connection to the power control network.

FIG. 2 shows the power components of processor cabinets 40 and 50 which were shown in FIG. 1. The power energization of the processor cabinets 40 and 50 is controlled by the power control card 80 shown in FIG. 2. The power control card 80 is controlled by a "system operator" through the cabinet control circuits via an "operator panel" 44, and by the operating maintenance personnel who work through the control display 45 (maintenance switches and indicators) within the processor cabinet.

The power control card 80 additionally monitors the cabinet environmental conditions such as over-temperature and cooling air-loss. This card is further described later under the title of "Power Control Subsystem".

The state of the cabinet power is further controlled by the power control network (PCN) through a card called the Power Net Slave Card 90. The processor cabinet (40, 50) also provides an AC power module 41 and a DC power module 43 for providing a high voltage DC to the attached-dependently-powered cabinets such as 20, 30.

Figure 3:
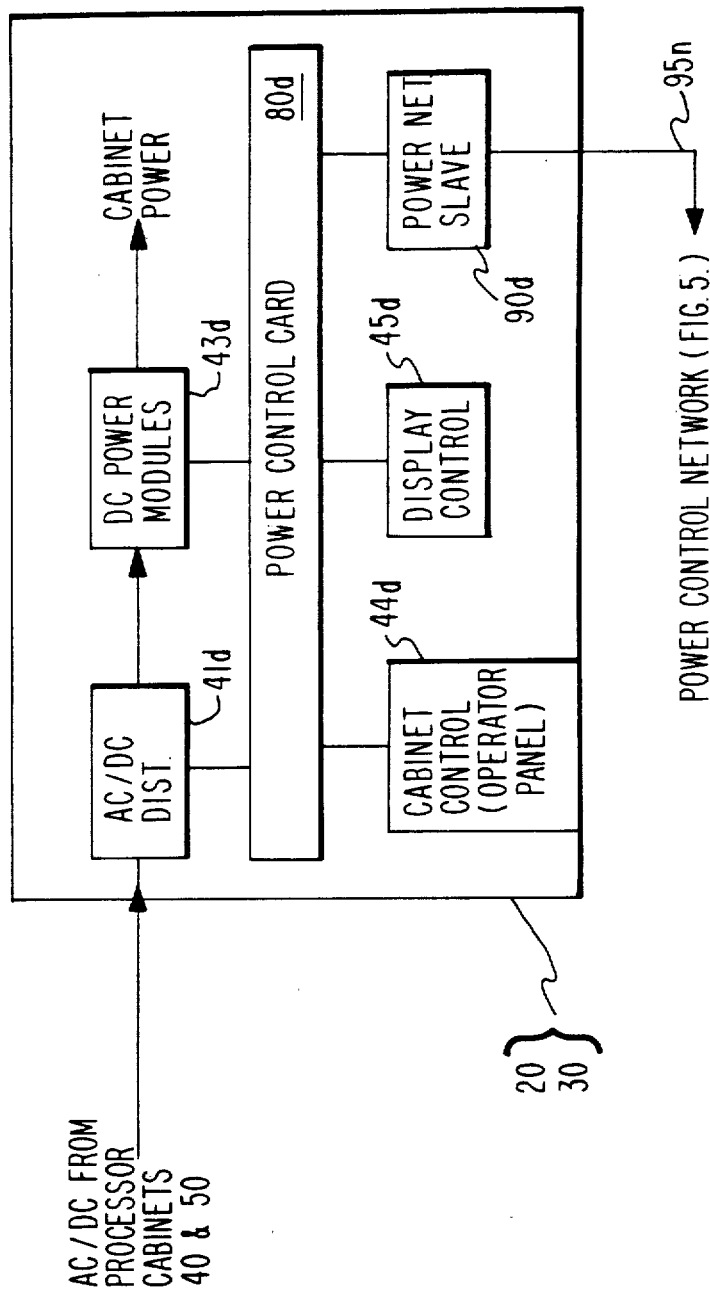
FIG. 3 shows a "dependently-powered" input/output cabinet in block diagram 4 and its connection to the power control network.

FIG. 3 illustrates the power components involved in the "dependently-powered" cabinets such as 20 and 30 of FIG. 1. The power for these "dependently-powered" cabinets is controlled by the power control card $80_d$. This power control card $80_d$ is controlled by a system operator (operating technician) through the cabinet control circuits and operator panel $44_d$, and also by the operating maintenance personnel through the control display $45_d$ (via maintenance switches and indicators) inside the cabinet.

The power control card $80_d$ also is used to monitor the cabinet environmental conditions such as over-temperature and the cooling air-loss.

The power in the dependently powered I/O cabinet of FIG. 3 is also controlled by the power control network through the power net slave card $90_d$.

As seen in FIG. 3 the "dependently-powered" I/O cabinet (such as 20 and 30) receive their AC and their high voltage DC input voltage from the attached processor cabinets such as 40 and 50 of FIG. 1.

Figure 4:
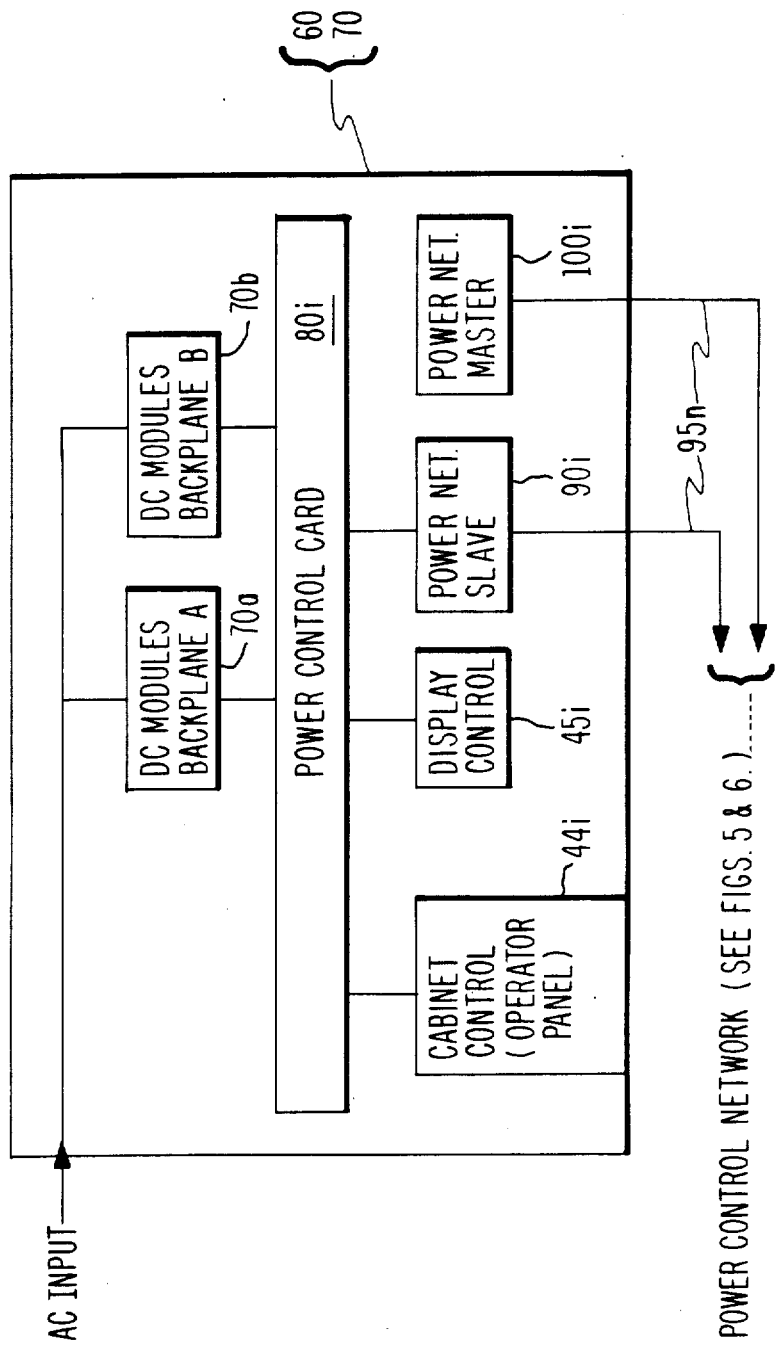
FIG. 4 is a block diagram showing an "independently-powered" cabinet and its connection to the power control network.

In FIG. 4 there is shown a block diagram of the various power components of the "independently-powered" cabinets such as 60 and 70 of FIG. 1. The power for these independently-powered cabinets is controlled by the power control card $80_i$. The power control card $80_i$ is controlled by a "system operator" through the cabinet control circuits and operator panel $44_i$, and also by the operating maintenance personnel through the control display $45_i$ (via maintenance switches and indicators inside the cabinet).

Likewise, as previously described, the power control card $80_i$ also monitors the environmental conditions in the cabinet such as over-temperature or the loss of "air". The cabinet power of the independently-powered cabinet of FIG. 4 is also controlled by the power control network through the power net slave card $90_{i\,i}$.

As seen in FIG. 4 the "independently-powered" I/O cabinets contain two I/O backplanes which are referred to as backplane A, $70_a$, and also backplane B, $70_b$, in addition to two interface panels described hereinafter. The DC power to each backplane is separately controlled. The DC power to both interface panels will be supplied the same as on backplane A, $70_a$.

The operator panel $44_i$ will provide separate controls for each backplane. The power control network (PCN) will also provide separate controls for each of the backplanes $70_a$ and $70_b$.

The DC power to each backplane is controlled separately. The operator panel $44_i$ will provide separate controls for each backplane and also the power control network connections $95_n$ shown in FIG. 4 will provide separate controls for each backplane.

Thus, the independently-powered cabinets will have their own AC power source and therefore may be considered as "free standing".

Additionally, the "independently-powered" memory cabinet may provide a remote support interface adapter. This adapter adds the power net master logic card to the cabinet as discussed hereinafter.

DESCRIPTION OF PREFERRED EMBODIMENT

Power Control Network (PCN):

To provide an integrated system, a Power Control Network (PCN, FIGS. 1 and 5, via $95_n$) connects all system cabinets. This allows a "SINGLE-POINT" of on-site operator control of the entire system of many cabinets. That is, the on-site operator need only depress a single power-on or power-off switch to control the entire system.

In addition to the single-point of on-site control, the PCN provides total "power control" from an external remote support center 300 via telephone connection. With the integrated PCN system, only a single remote connection is needed to drive the entire system.

In addition to the basic power on and off control functions, the PCN provides a number of system failures and status monitoring functions and system maintenance controls. These functions are described in paragraphs that follow.

The PCN allows the capability for an UNATTENDED site, that is, no local system operator is required. All system power controls, failure condition monitoring, and maintenance controls are available via the PCN to the remote center, 300.

The PCN is specifically implemented through power net slave cards contained in each system cabinet and interconnected to the PCN. Each slave card is "always" powered, that is, it is powered if the AC breaker for its cabinet is on. The slave within a cabinet is powered whether the cabinet operating DC power is on or not.

Figure 8:
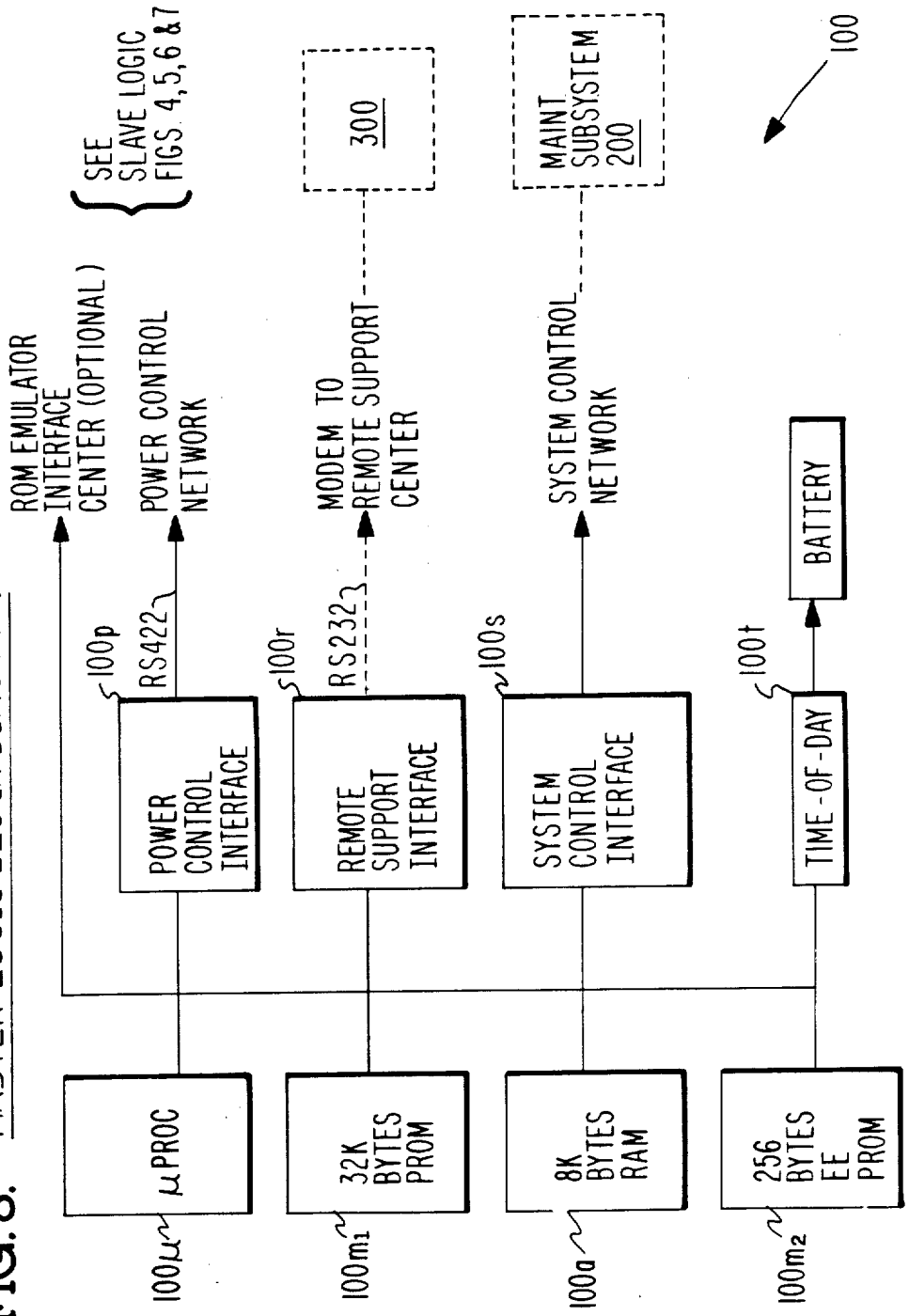
FIG. 8 is a block diagram of the master network power logic unit showing the interconnections to the other parts of the system network.

The power net master logic card 100 of FIG. 8, which is part of the before mentioned remote support interface adapter (contained within an independently-powered memory cabinet), drives the Power Control Network and therefore all the power net slaves. The master logic unit 100 provides the central hub between the power control functions (Power Control Network), the remote support center (300) telephone connection and the system maintenance (200, FIG. 8) subsystem. The master card 100 is also "always" powered.

TABLE I

OPERATOR PANELS

Operator Control Panels

The Operator Control Panels 44, 44$_d$, 44$_i$, FIGS. 2, 3, 4, are accessible to the operator on the outside of the respective cabinets. The panels provide the following functions:
PROCESSOR CABINET OPERATOR PANEL (44)

POWER-ON/POWER-OFF indicator & switch.
CABINET/SYSTEM MODE indicator & switch.
POWER FAIL/AIR LOSS indicator.
DEPENDENTLY-POWERED I/O CABINET OPERATOR PANEL (44$_d$)

POWER-ON/POWER-OFF indicator & switch.
CABINET/SYSTEM MODE indicator & switch.
POWER FAIL/AIR LOSS indicator.

INDEPENDENTLY-POWERED MEMORY CABINET OPERATOR PANEL (44$_i$)

POWER-ON/POWER OFF BACKPLANE A indicator & switch.
POWER-ON/POWER OFF BACKPLANE B indicator & switch.
CABINET/SYSTEM MODE indicator & switch.
POWER FAIL/AIR LOSS indicator.
REMOTE MODE ENABLE key switch.

INDEPENDENTLY-POWERED I/O CABINET OPERATOR PANEL (44$_i$)

POWER-ON/POWER-OFF BACKPLANE A indicator & switch.

POWER-ON/POWER-OFF BACKPLANE B indicator & switch.
CABINET/SYSTEM MODE indicator & switch.
POWER FAIL/AIR LOSS indicator.

(A) Cabinet Power Control Functions:

The cabinet power control circuitry controls and monitors all the power modules of the various cabinets. It also monitors the various cabinet environmental conditions such as over-temperature, etc.

The power control circuitry of the network system can be controlled from three sources:

(1) by the operator through the cabinet operator panel 44;
(2) by maintenance personnel through the control display 45;
(3) by the power control network through the network interface slave as will be discussed in connection with FIG. 5.

The operator panel control switches, in element 44, are active only when the cabinet is in the "cabinet mode" with the exception of the processor's power-on/power-off functions, and the cabinet/system switch. Table I indicates the switches for both the cabinet mode or system mode.

The maintenance switches are active only when the cabinet is in the "cabinet mode".

The power control network drive functions (the switch type functions) are active only when the cabinet is in the "system mode". The power control network monitor functions (that is the status) are always valid.

When a cabinet is changed from the "system" to the "cabinet" mode, the power state of the cabinet will not change, except that marginal conditions will follow the cabinet margin switches.

When a cabinet is changed from the "cabinet" to the "system" mode, the power state of the cabinet will follow the external power control signals derived from the slave units, as 90, 90$_d$, 90$_i$, etc.

(B) Functions of the Cabinet Maintenance Power Control:

Maintenance personnel can control the following maintenance functions from the control display 45 (FIGS. 2, 3, 4) within a cabinet:

(a) Margin indicators; these are used to indicate that the associated logic voltages within the cabinets are in a marginal high or marginal low state;

(b) Margin switches—these will manually set the associated logic voltages within the cabinet to the marginal high or marginal low state. These switches are active in the "cabinet" mode only;

(c) Power fail indicators—these indicate that a power failure has occurred in one of the power modules within the cabinet. This indicator is valid in either the "cabinet" or in the "system" mode;

(d) Over temperature/air loss failure indicators—will indicate an over temperature or an air loss condition in the cabinet. This indicator operates in either the cabinet or the system mode;

(e) Power fault indicators—these will indicate faults in the various power modules in the cabinet and they will operate validly in either the "cabinet" mode or the "system" mode.

(C) Operator Power Control Functions:

Certain functions are controlled by the "system operator" from the cabinet control operator panel 44. These are:

(1) Power-on/power-off switch indicator: in the "cabinet" mode this switch controls the state of the cabinet power (on or off). In the "system" mode this switch is inactive except for the processor cabinet switch. The processor power-on/power-off switch, in the "system" mode, acts as system control switches. Activation of this switch in the "system" mode will cause a "power-on" request or a "power-off" request to be sent to the power control network. The network may then drive the power-on or drive the power-off to all system cabinets which are in the "system" mode. All cabinet "power-on/power-off" indicators are valid for either the cabinet mode or the system mode.

(2) The cabinet/system mode switch: this controls the "mode" of the cabinet. This switch is always active whether the cabinet is in the "cabinet" mode or the "system" mode.

(3) Power fail/air loss indicators: these indicate the respective failure conditions within the cabinet and the indicators are valid in either the cabinet mode or the system mode;

(4) Remote enable switch: this key lock switch enables the connection to be made to the remote system support center 300. This key switch is active in either the cabinet mode or the system mode.

(D) Power Control Network (PCN) Functions:

Table I and paragraph C above described the functions that an on-site operator can control via the operator panels 44 for each cabinet. Paragraph B above described the additional functions that a maintenance engineer can control from the maintenance panels "internal" to each cabinet. The Power Control Network allows remote control of all the above mentioned functions. In this context, "remote" means distant from a cabinet, that is, single-point on-site control; or distant from the site itself, that is, via telephone connection.

Each system cabinet is uniquely addressable over the Power Control Network (PCN). PCN commands are actions to a cabinet driven by the PCN. PCN commands can only affect a cabinet when it is in "system" mode, described in paragraph A above. PCN status is information about the cabinet returned over the PCN. PCN status is available in either "system" or "cabinet" local modes. For cabinets with separately controllable backplanes, the PCN functions are selected separately for each backplane.

The PCN (Power Control Network) functions are:

(1) Power-On Command: Turns the addressed cabinet to power on.

(2) Power-Off Command: Turns the addressed cabinet to power off.

(3) Reset Command: Resets, clears any power fault conditions within the addressed cabinet.

(4) Set Margins Commands: Sets voltage margins conditions within the addressed cabinet for the selected voltage source to either high or low states. This is controllable for the +5 VDC, −2 VDC and −4.5 VDC supplies.

(5) Send Status Command: Requests the addressed cabinet to send specified "status" information over the PCN.

(6) Miscellaneous Control Bit Commands: Command activates or deactivates four external signals which may be used to control clock or other sources in dual processor systems.

(7) Power-On/Off Status: Indicates the power "on or off" state of the addressed cabinet.

(8) System/Cabinet Mode Status: Indicates whether the addressed cabinet is in "cabinet" local mode (no "external" control allowed) or "system" mode (external control via PCN allowed).

(9) Over-Temperature Failure Status: Indicates that the addressed cabinet has experienced an over temperature condition and is shut down.

(10) High-Temperature Warning Status: Indicates that the addressed cabinet is running under conditions outside of range and over-temperature failure may be imminent.

(11) Air Loss Failure Status: Indicates that the addressed cabinet has lost cooling fan(s) and is shut down.

(12) Power Fault Status: Indicates that the addressed cabinet has experienced a power supply fault condition and is shut down. This is reported for the +5 VDC, −2 VDC, −4.5 VDC, +−12 VDC and 15 KW supplies.

(13) Voltage Margin Status: Indicates a specific voltage supply is running in a margin condition. This is reported for +5 VDC, −2 VDC, and −4.5 VDC supplies in both high and low conditions.

(14) Power-On Request Status: Reported only by processor cabinets in "system" mode. It indicates that the power-on switch was depressed by the operator. In system mode, this switch is the power-on switch for the entire site.

(15) Power-Off Request Status: Reported only by processor cabinets in "system" mode. It indicates that the power-off switch was depressed by the operator. In system mode, this switch is the power-off switch for the entire site.

Figure 5:
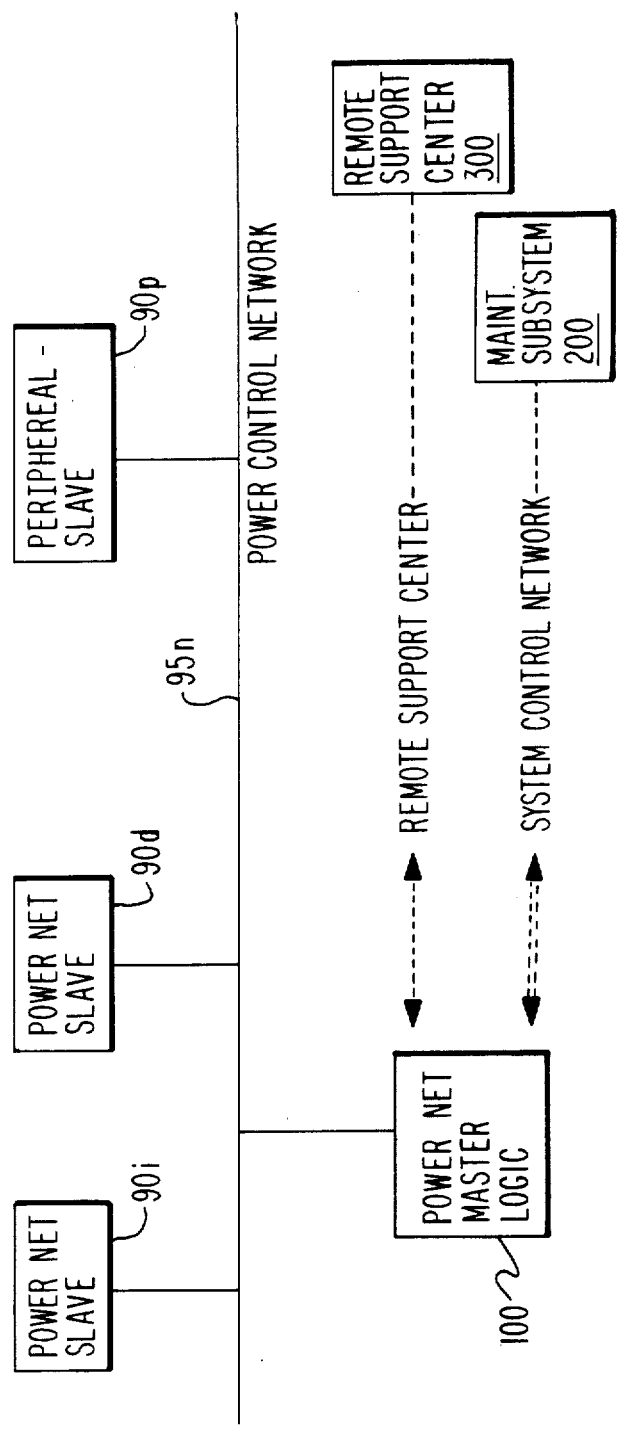
FIG. 5 is a basic block diagram of the power control network showing the central power net master logic unit connected to control various power net slave logic units in this system.
Figure 6:
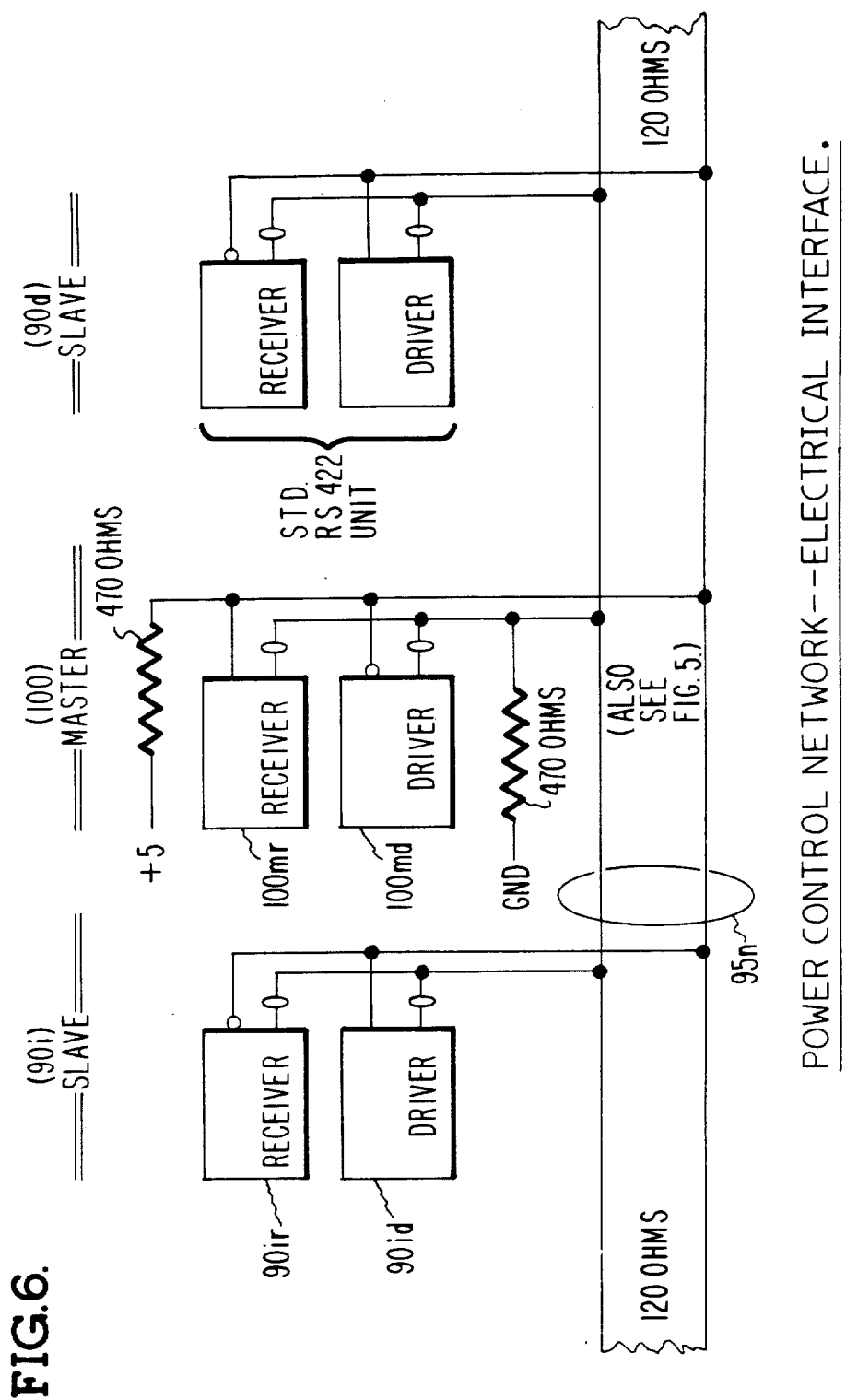
FIG. 6 is a block diagram showing the interconnection between the master logic unit and the slave logic units in the system.

Power Control Network Electrical/Mechanical Characteristics:

The PCN shown in FIGS. 5 and 6 is serially routed, two-wire, twisted-pair. The PCN circuit uses RS422 standard differential drivers and receivers (FIG. 6).

Connected on the PCN will be numerous power net slaves and peripheral slaves and one power net master. The total number of connections is 64. The maximum transfer rate may reach 10K bits/second.

FIG. 6 shows the connection of the RS422 drivers and receivers for slave cards and the master card. Also shown is the network termination resistors of 120 and 470 ohms.

Each slave and master card provides two PCN (Power Control Network) connectors. One connector receives the PCN cable from the previous unit and the other connector sends the PCN cable to the next unit. The PCN is thus serially routed.

For PCN connections between units within attached cabinets, the PCN cable is a simple, inexpensive, twisted-pair cable.

For PCN connections to non-attached cabinets, the PCN cables first are routed through interface panel cards in an I/O cabinet through RFI shielded cable into the non-attached cabinet.

Figure 7:
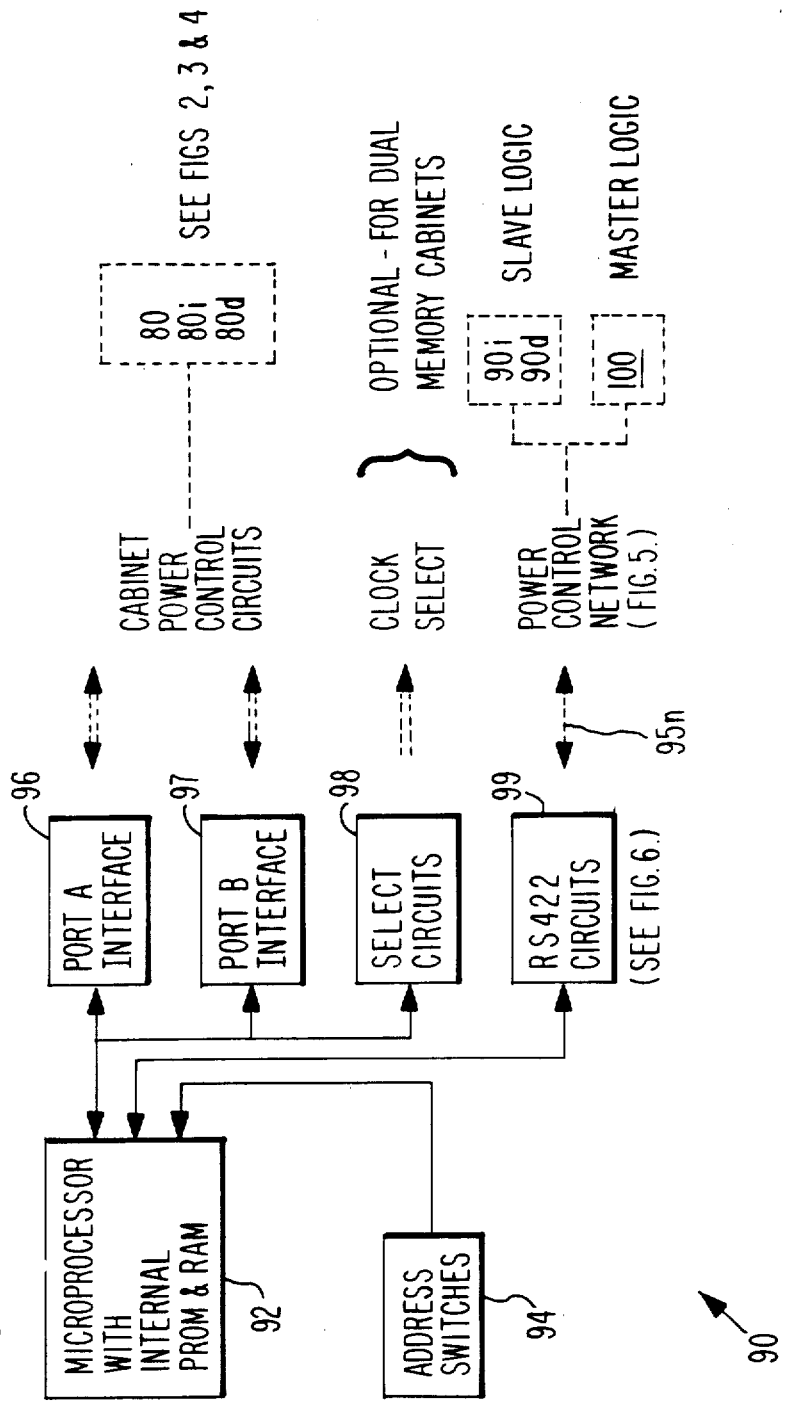
FIG. 7 is a block diagram of a typical power slave logic unit.

FIG. 7 shows a block diagram for a power net slave card. The diagram shows the controlling microprocessor 92 and the address switches 94 which give each cabinet an unique PCN address. Each slave has two parallel connecting ports 96, 97 to the power control cards of its cabinet. The slave also provides, via circuit 98, clock select or other signals and connects the RS422 interface to the PCN network itself.

Figure 9:
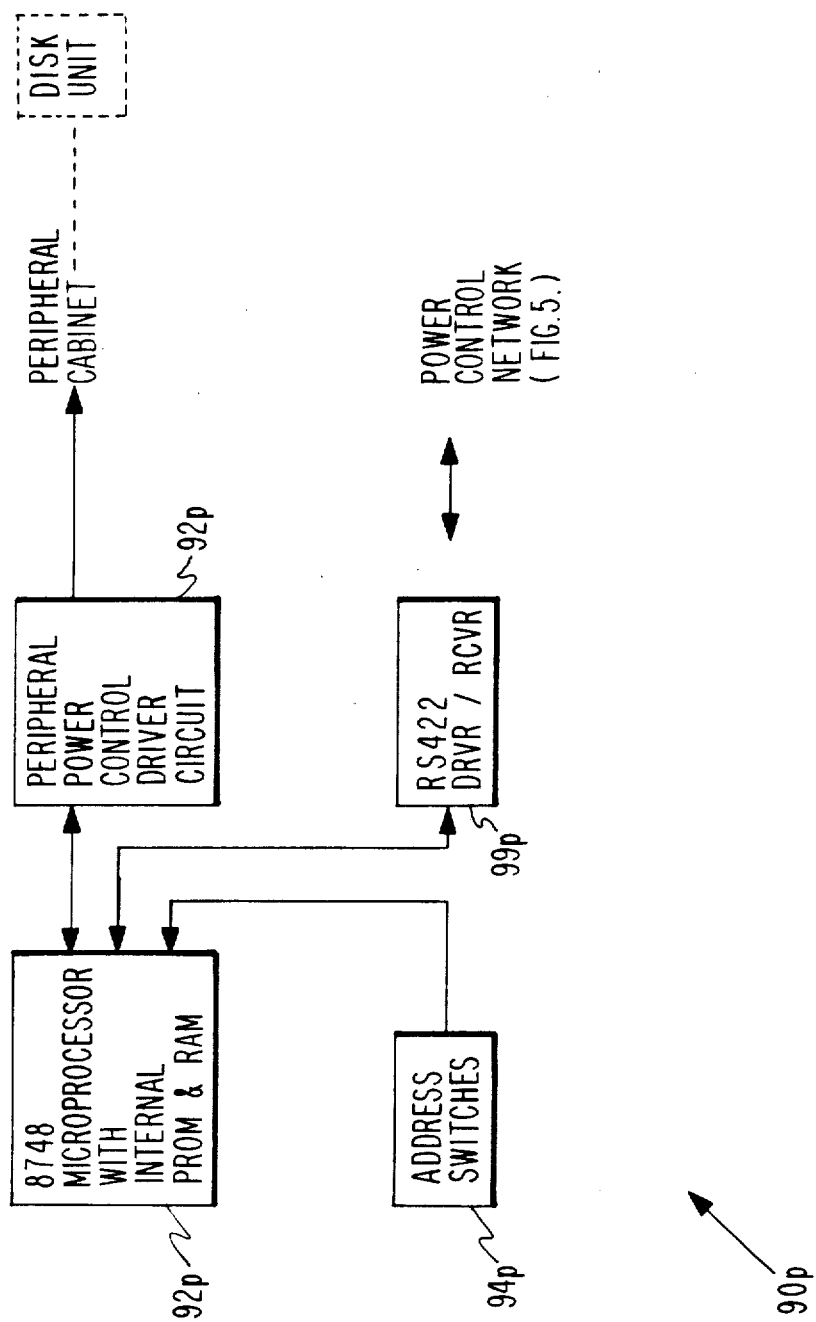
FIG. 9 is a block diagram of the peripheral power slave logic unit showing its connection to a peripheral cabinet and to the power control network of FIG. 5.

FIG. 8 shows the power net master logic unit 100 card block diagram, and FIG. 9 shows a peripheral-slave card block diagram. This slave can control only the power-on and power-off of a peripheral cabinet (disk pack controller).

Power Network Slave Logic:

As seen in FIG. 7, the power network slave logic shows a logic card connected between the power control circuits of a cabinet and the power control network.

A major element of the slave logic card is a microprocessor such as an 8748 chip which contains internal program PROM and internal RAM. A typical chip of this designation is manufactured by Intel Corporation, whose address is 3065 Bowers Avenue, Santa Clara, Calif., and wherein this chip is described in a publication entitled "Microcontroller User's Manual", Order #210359-001, copyright 1982, and published by Intel Corporation, Literature Dept. SU3-3, of 3065 Bowers Avenue, Santa Clara, Calif.

Each slave logic unit has a unique address which is set within the card by means of switches shown as element 94, address switches, in FIG. 7. The slave logic is connected to the power control network of FIG. 5 using the circuits shown in FIG. 6, which are RS422 receiver and driver chips. The RS422 receiver and driver chips are those such as typically manufactured by Advanced Micro Devices Company of 901 Thompson Place, (P.O. Box 453), Sunnyvale, Calif. These circuits are described in a publication entitled "Bipolar Microprocessor Logic & Interface Data Book" published by Advanced Micro Devices Company, copyright 1983.

The power network slave logic in FIG. 7 has two ports designated as port A interface 96 and port B interface 97. These interfaces connect to the power control circuits within each of the cabinets such, for example, as power control card 80 of FIG. 2, power control card 80$_d$ of FIG. 3, and power control card 80$_i$ of FIG. 4. The signals to and from the port A96 and port B97 are described hereinafter.

The power network slave logic unit 90 has four output signals (shown in FIG. 7 at the extreme right side) which may be activated or deactivated under the control of commands sent over the power control network. Thus, these four output signals may be used in cabinets containing a DPM (dual port memory), or for independent memory cabinets, in order to select the source for the DPM clocks. These four signals are individually controlled, raised or lowered, by commands from over the power net from the power net master logic unit 100 of FIG. 5.

These four output signals are driven by the slave logic of FIG. 7 by means of high-drive transistor type logic (TTL) inverter buffer chips. The output physical connection to the slave logic unit card is by "slip-on" posts to which clock-type, backplane type coaxial cables can be attached. A grounded post is provided with each signal post.

Thus, the Select Circuits 98 of FIG. 7 use the inverter-buffer chips to provide a signal from the slave logic over a coaxial cable over to the DPM (Dual Port Memory) back plane.

The power network slave logic unit 90 requires the use of control signals or "always power" from the cabinet in which it resides.

Two on-board indicators and one switch are used to control each of the power network slave logic units 90, 90$_i$, 90$_d$, 90$_p$. A push-button switch (the re-set switch) is used to initialize the slave logic to run its own "self-test". This is the same function that occurs at slave power-up time. One indicator (self-test) is "on" when the slave self-test program is in operation. If a self-test error occurs, this indicator will remain "on".

The second indicator (NET ERROR) is "on" whenever the slave logic detects a "NET" problem while the slave is communicating on "NET". These NET errors include a framing error (too few or too many discs), a parity error, a NET protocol error, and an invalid command. The "NET ERROR" indicator will be deactivated when a "good" net communication to the slave logic unit occurs.

Power Network Master Logic:

A block diagram of the power network master logic is shown in FIG. 8. The power network master logic 100 of FIG. 8 is housed in an independently-powered memory cabinet within the system, such as cabinet 70 of FIG. 1. The power network master logic will require power from this cabinet.

The master logic 100 is the controlling device on the power control network of FIG. 5. It initiates all communications over the network; and thus, all communications over the network are effectuated between the master 100 and a slave logic unit such as 90. There is only one "active" master logic unit, such as 100, which may be connected to the power control network of FIG. 5 at any given time.

The network master logic 100 also interfaces to the Maintenance Subsystem (200 shown in FIG. 8) through the System Control Network shown in FIG. 5. Also, as indicated in FIG. 5, the power network master logic is the single point of connection of the system to a Remote Support Center (RSC, 300 in FIGS. 5 and 8).

FIG. 8 also shows the connections to the Remote Support Center 300 and also to the power control network of FIG. 5.

As seen in FIG. 8, the power network master logic unit 100 is provided with a microprocessor 100$_u$ to which are connected a PROM 100$_{ml}$ and EEPROM 100$_{m2}$ in addition to a RAM unit 100$_a$. A power control interface 100$_p$ connects the microprocessor to the power control network and a remote support interface 100$_r$ connects the microprocessor to the remote support center 300. A time of day circuit 100$_t$ with battery back-up provides time signals for the unit.

The power network master logic unit 100 of FIG. 8 provides a central interconnection point for the power control network of FIG. 5, in addition to the system control network which is connected through the interface 100$_s$. It is also the central interconnection point for the remote support center interface (remote diagnostic) of element 100$_r$.

The power network master logic unit 100, as the master unit for the power network, controls all the actions on this network.

In any multi-processor system, there may be only one "active" power network master logic unit. Since, however, this unit is of considerable importance to the system operation and maintenance, there is generally provided a spare power network master logic unit, even though a failure in the power subsystem will not affect the operation of the overall processing unit.

The microprocessor 100$_u$ (Intel 8088) of FIG. 8 may be set to run at 8 megahertz. It executes its code out of the 32 K bytes of PROM 100$_{ml}$. The 8K bytes of RAM 100$_a$ are used for data buffers and for operating stacks. The 256 bytes of electrically erasable PROM 100$_{m2}$ are used to store configuration-dependent option flags. The time of day circuit 100$_t$ is backed up by a battery for use during times of power failure. Six indicators and five switches are provided on the master logic unit 100 for maintenance of the master card itself.

Peripheral Slave Power Control Adaptor:

As seen in FIG. 5, the power control network may include peripheral devices which are provided with a peripheral slave power control adaptor $90_p$.

FIG. 9 shows a block diagram of such a peripheral slave power control adaptor $90_p$. Provided therein is a microprocessor $92_p$ which connects to a peripheral power control driver circuit $95_p$ having connections to the peripheral cabinet. Also provided are address switches $94_p$ which provide an input to the microprocessor $92_p$, and also a driver-receiver circuit $99_p$ which connects to the power control network of FIG. 5.

The peripheral slave power control adaptor, such as $90_p$ of FIG. 9, is located in an interface panel within the I/O cabinets such as 60 and 70 of FIG. 1, and also in cabinets 20 and 30 of FIG. 1.

The peripheral slave power control adaptor $90_p$ of FIG. 9 connects between the power control network of FIG. 5 and any selected system peripheral cabinets. There are certain cabinet types to which the peripheral slave power control adaptor may be connected. These are:

(a) a disk pack controller (without status signals)
(b) a disk pack controller (with status signals)
(c) a disk pack exchange unit (without status signals)

The peripheral slave adaptor $90_p$ provides only "power-on" and "power-off" control for these cabinets.

The peripheral slave adaptor $90_p$ is logically a simple slave unit. The microprocessor $92_p$ may use an 8748 microprocessor chip (previously described) and interfaces to the power control network with the RS422 driver receiver chip designated $99_p$.

The peripheral slave logic of FIG. 9 differs from the internal power slave logic unit of FIG. 7 in that, in place of the port A and port B interfaces (96, 97) of FIG. 7, the "peripheral" slave logic has special driver circuits $95_p$ in order to control the "on/off" state of the connecting peripheral cabinets.

Power Control Network Communications:

All commands and communications over the power control network are initiated by the power net master logic unit 100 of FIGS. 5 and 8.

FIG. 10 is an illustrative drawing showing the particular sequence of events over the network. The master logic unit 100 first sends the Address byte shown in line 1 of the drawing of FIG. 10. This Address is the address of the desired slave unit to be addressed. Each slave unit receives and evaluates the Address received and then the appropriate slave unit will return its Address to the master power unit 100.

If the "correct" slave address is returned to the master power logic unit 100, as shown in line 2 of FIG. 10, then the master logic unit 100 will send a Command byte (shown in line 3) to the previously addressed slave unit, such as 90 of FIG. 7.

The slave unit, such as 90, then returns the Command byte to the master as illustrated in line 4 of FIG. 10. Thus, when the slave has received the Command byte, it returns it to the master and if the byte received by the master logic unit 100 then agrees with the byte that it (master unit) had previously sent, the master logic unit 100 re-sends the Command byte again, as illustrated in line 5 showing the Command byte being re-sent from master to slave.

If the second Command agrees with the first Command byte, the slave logic unit 90 will decode and execute the Command received. The slave will then return its General Status byte to the master as seen in line 6 of FIG. 10.

If the Command was a Send Status Command, then the specified Status byte is returned instead of the General Status byte.

If the command sent by the master logic unit 100 to a slave logic unit 90 was either a "power-on" or a "power-off", then the General Status byte which is returned to the slave logic unit 90 will not reflect the new power state of the cabinet involved. It will show the status of the cabinet "prior to" the command. To check the new state of the cabinet involved, a Send Status Command will be sent about 15 seconds later after the power on/off Command was sent.

Thus FIG. 10 indicates the general network flow for the master power logic unit 100 as it polls the various slaves 90 over the network. After the master logic unit 100 sends an Address, it waits for the return of the addressed slave unit's address. If an incorrect address is returned from the slave logic unit 90, the master power logic unit 100 will re-try the expected address. It will try the desired address three times before it assumes that the Address slave logic unit 90 may be "bad".

The master power logic unit 100 also does the same re-try/time-out procedures for the Command bytes. When the master power logic unit 100 finds an "improperly" responding slave logic unit 90, while polling, it will report the condition to the maintenance subsystem 200 over the system control network connected as shown in FIG. 8.

FIG. 10 also indicates the network byte format for the power network. As shown therein, there is one bit used for a start bit, then 8 bits are used for a data byte, then one bit is used for odd parity, and one bit is used as a stop bit.

Figure 11:
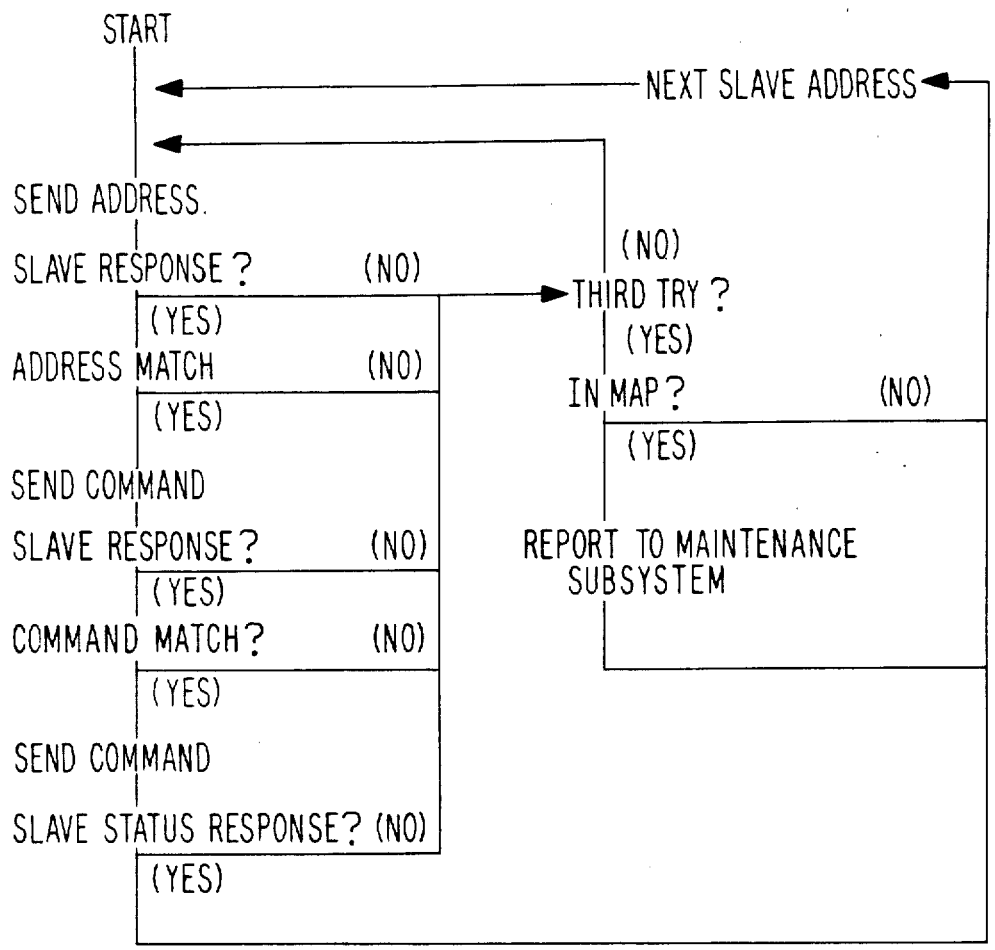
FIG. 11 is a flow diagram which summarizes the protocol activity for the master power network logic

FIG. 11 shows a drawing of a flow chart showing the network flow for the master power control logic unit 100 which summarizes the various protocol steps used in FIG. 10 on lines 1-6.

Figure 12:
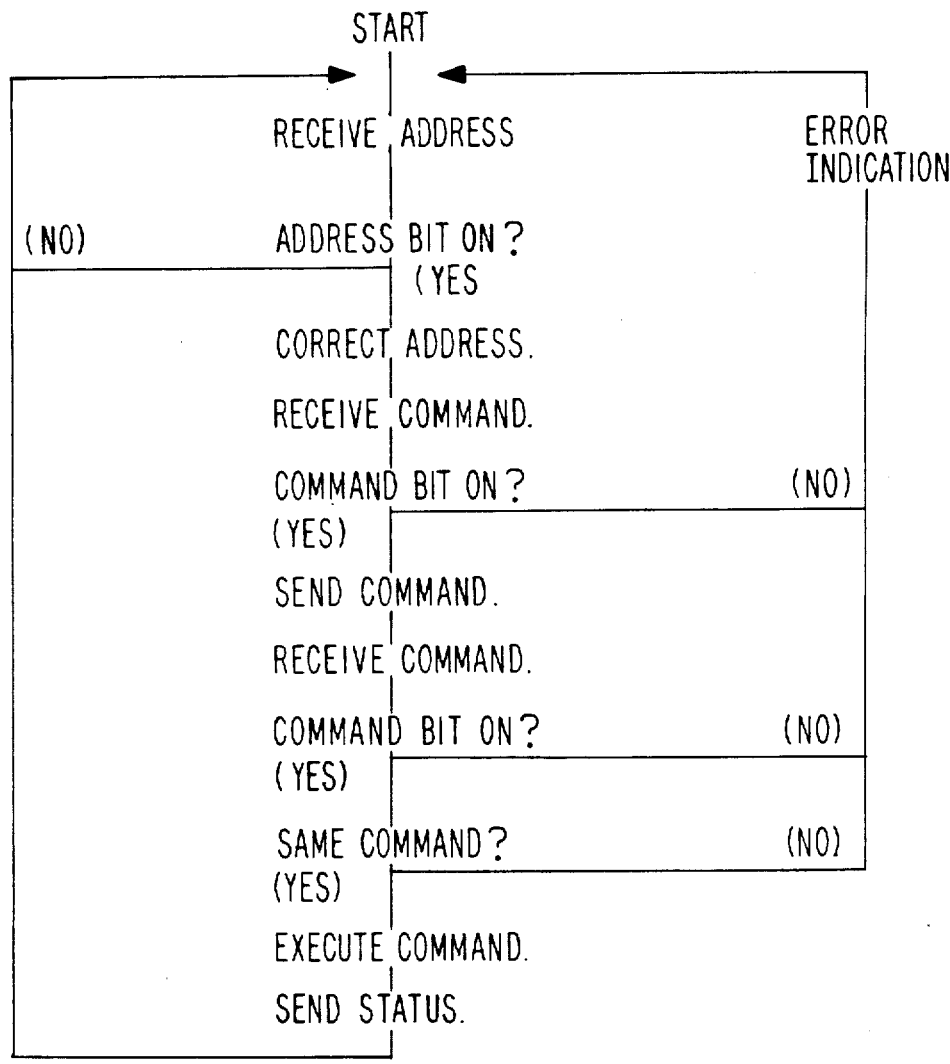
FIG. 12 is a flow diagram which summarizes the protocol activity of the slave power control logic unit.

FIG. 12 is a flow chart diagram which summarizes the protocol involved for the slave power logic unit in the system operation.

Table II shows one scheme on which Addresses may be provided for the processor cabinets, the independent memory cabinets, the I/O cabinets, and the various peripheral cabinets, whereby the power control network system may address and communicate with specific cabinets in order to provide Command and Control functions in the power network system.

POWER NETWORK ADDRESS BYTE DEFINITIONS

TABLE II

| Address Bits | | |
|---|---|---|
| 7654 | 3210 | |
| 1000 | 0000 | Power Control Network (Maintenance only) |
| 1000 | 00xx | (Spare) |
| 1000 | 01xx | Processor Cabinets |
| 1000 | 1xxx | Independently-Powered Memory Cabinets |
| 1001 | xxxx | Dependently-Powered I/O Cabinets |
| 101x | xxxx | Independently-Powered I/O Cabinets |
| 1100 | 1xxx | Disk Exchange Cabinets |
| 1101 | 0xxx | Disk Controller Cabinets |
| 1101 | 1xxx | Disk Controller Cabinets - Memorex Type |

Note: Only 64 connections are allowed on the network.

Power Control Network Protocol:

Since the PCN has "great power" over a system, that is, it can turn off a system, it is necessary that the network protocol be fault tolerant and reliable. The PCN protocol was designed with several layers of redundancy and checking.

FIG. 10 shows the PCN byte format. The PCN byte contains one start bit, eight bits of information (data byte), one odd-parity-bit, and one stop bit.

FIG. 10 also shows the PCN message transfer protocol between the power net master card and a slave card. All transfers on the PCN are initiated by the master. All transactions follow the steps described below:

(1) Master sends an address byte to all slaves. An address byte has a "one" in the most significant bit position. Each slave compares the address byte to its address switches. Each slave has an unique address and that address values are predefined and grouped to also indicate that type of cabinet in which the slave is located. The master program can generate an address or pull an address from memory $100_a$ of FIG. 8. The master program gives the address to microprocessor $100_u$ which transmits it from master logic 100 to slave units 90, $90_d$, $90_i$, etc. via the network lines of FIG. 6.

(2) The slave, whose address switches equal the address byte value, then returns its address over the PCN to the master. The master checks the received value with the sent value to ensure the proper cabinet is responding. Thus, the slave program receives the transmitted address when it matches its own unique address and retransmits its address via the network of FIG. 6. The program gets its address from the settable address switches 94 of FIG. 7. The master program in the master logic unit compares the received-back address which comes through $100_p$ of FIG. 8. This address came from the slave unit 90 (or $90_d$ or $90_i$, etc.) via FIG. 6.

(3) The master then sends a command byte to the addressed slave. A command byte has a zero in the most significant bit position. The master program can generate an instruction or pull one from memory $100_a$ of FIG. 8 in the master logic unit. The microprocessor $100_u$ will instruct $100_p$, FIG. 8, to transmit it via the circuit of FIG. 6.

(4) If the command is a good command, the slave returns the command over the PCN. The slave logic unit receives the instruction and the slave program checks the instruction for validity, then retransmits the instruction (if valid) via the circuit of FIG. 6 back to the master unit 100.

(5) The master compares the returned command with the sent command; if it compares accurately, it re-sends the command byte to the slave. Thus, the master program then causes the master logic unit 100 to compare the "returned-instruction" from slave unit 90 with the originally sent instruction. When these two instructions are verified as being in agreement, the program instructs master logic unit 100 to transmit the instruction again over to the addressed slave unit via $100_p$ of FIGS. 8 and 6.

(6) The slave compares the second command byte with the first command byte; if they agree, it checks the command, and if valid, the slave will begin execution of the command. Thus here, the slave unit receives the instruction for the second time and the slave unit program compares this instruction with the originally received instruction whereupon (if both instructions coincide) the slave unit generates control signals. These generated control signals are placed on circuits 96, 97 or 98, FIG. 7 (depending on the instruction) and especially to the Power Control Card $80_i$ (FIG. 4) or to $80_d$ (FIG. 3) or 80 (FIG. 2) via the port interfaces 96, 97 of FIG. 7. In the case of the peripheral slave unit $90_p$ (FIG. 8), the slave unit generates a pulse which is sent to the peripheral cabinet (disk control unit of FIG. 9) via circuit $95_p$.

(7) In response to the second command byte, the slave returns a status byte of information to the master. The normal status byte returned contains "general status" information about the cabinets condition: on/off, system/cabinet local modes, any failure condition, any margin condition, on/off request. If the command was a "send status" command, the slave will send the specific information desired: specific margin conditions, specific cabinet power failure conditions, clock select signal states. Thus, after generating the needed control signals, the slave unit will get "cabinet status" information via circuits 96, 97 of FIG. 7. This information creates the "general status" byte (or other status byte depending on the instruction from the master unit 100). The slave unit (90, $90_d$, $90_i$, etc.) will then transmit the status information to the master unit 100 via, for example, the driver $90_d$ of FIG. 6. When the master unit 100 gets the status information (via $100_p$ of FIG. 8), the master program can act on the basis of the type of information it received.

(8) One additional safety check is performed by the master card on the status byte returned. Since power-on request and power-off request status bits are so critical to the entire system, these status bits are double-checked if they are returned in the general status byte. This is done as follows:

(a) A "send status" command is sent; the general status byte is received for the second time to see if the power-on/off request status bit is still active.

(b) A reset command is sent to the slave in question. This clears the power-on/off request bit.

(c) A "send status" command is again sent (the request status should now be inactive).

(d) If each step above was correct, the master will execute the power-on or power-off request sequence to the system.

Any time-outs or miscompares, in any of steps 1–8 above, abort the transfer and prevent the execution of any action to cabinets in the system. FIG. 11 gives the master flow (less steps a–d). FIG. 12 gives the slave flow.

Power Control Subsystem

The power control subsystem shown in FIGS. 13, 14, 15 and 16 is used to controllably sequence various power supply modules either "on" or "off" and to detect failures in the power modules or cooling systems that could damage the logic cards, interfaces or memory storage devices.

Figure 13:
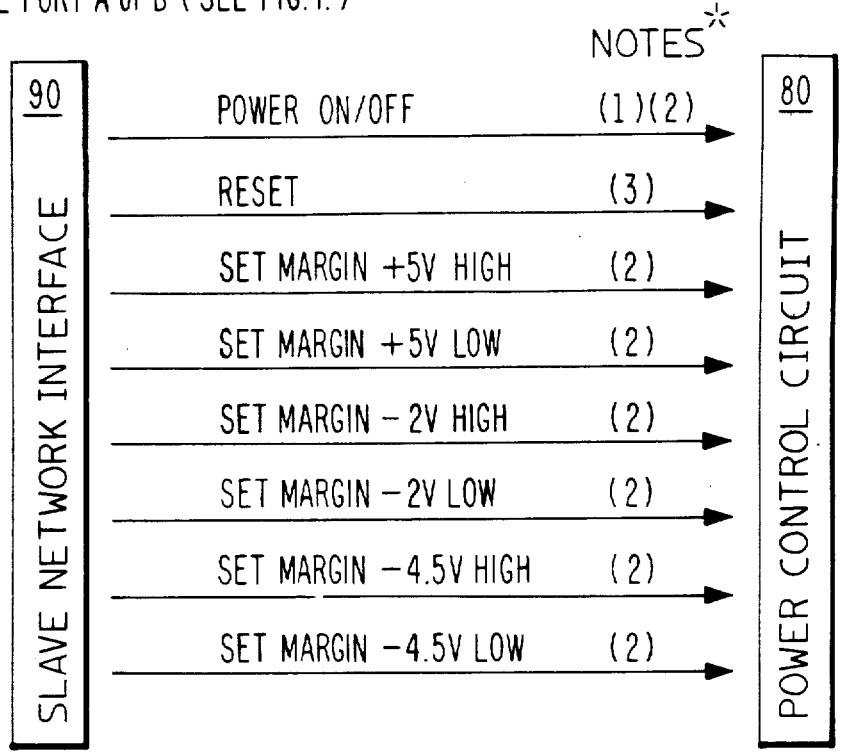
FIG. 13 is an illustration showing the output signals from the slave logic to the power control circuit.

The power sequence control and failure detection is oriented around the power control circuit card 80 ($80_i$, $80_d$) in conjunction with its interface to the slave logic units 90 ($90_i$, $90_d$) as shown in FIGS. 13 and 14. FIG. 13 shows the output control signals from the slave logic 90 to the power control circuit 80. Then FIG. 14 shows the various "indicator" signals which the power control circuit provides to the slave logic 90.

In order to control each power supply module on or off, a transistor type logic (TTL) compatible signal is sent to each power supply module from the power control circuit card 80, aocording to instructional data received from the slave logic unit 90.

Each power supply module (as 41, 43, 70$_a$, 70$_b$, of FIGS. 2, 3, 4) will send a TTL signal back to the power control circuit 80 (80$_i$, 80$_d$) to indicate if that module failed or was under voltage, over voltage, over current or over temperature. Thus, the over temperature or air loss sensors of FIG. 15 can send failure signals to the sequencer 80$_q$ in power control circuit 80.

Figure 16:
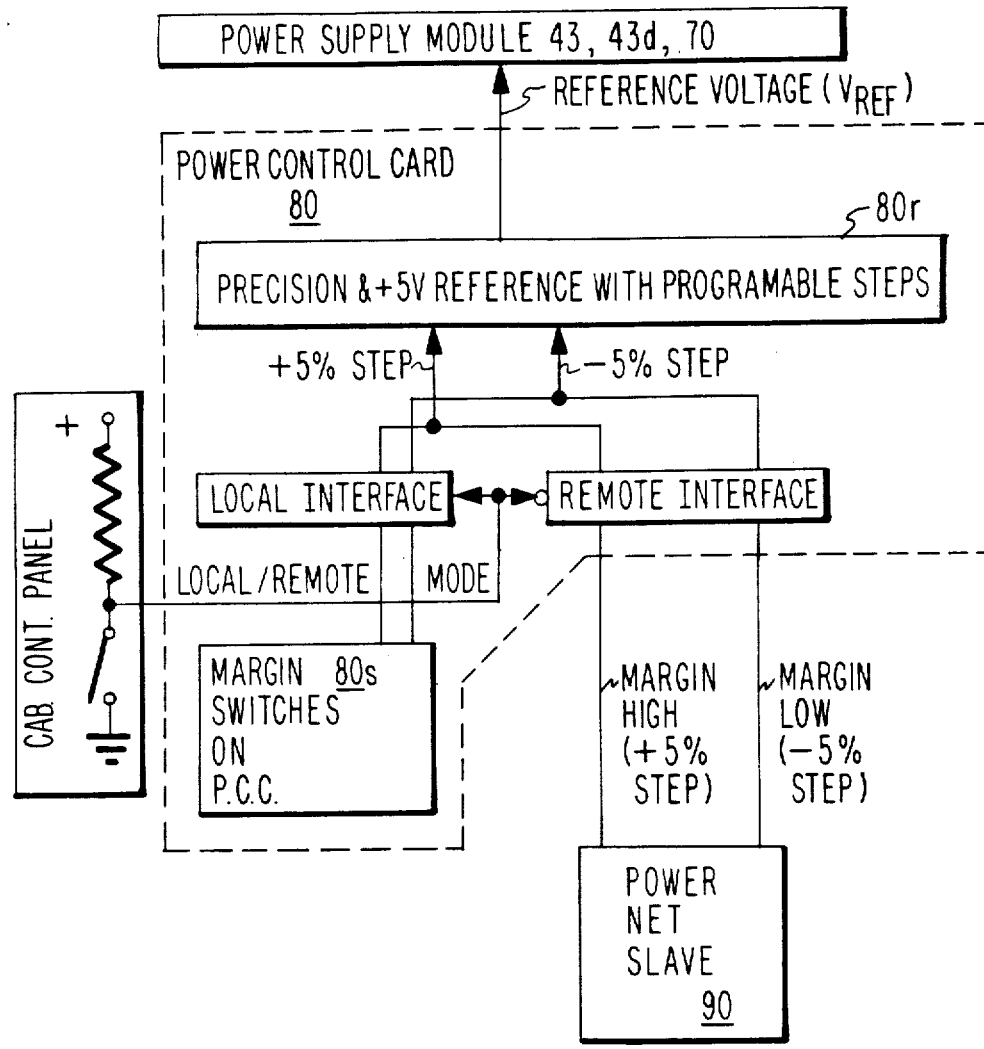
FIG. 16 is a block diagram illustrating the circuitry for margin control voltages in local and remote modes.

As indicated in FIG. 16, a precision reference voltage unit 80$_r$ has programmable voltage steps of + (plus) or − (minus) 5 percent which can be controlled by input signals via a local interface from margin switches 80$_s$, or via a remote interface from slave logic 90. This permits "margining" of the output voltages on each power supply module.

The voltage output of the logic power supplies (+5 V, −4.5 V and −2.0) can thus be adjusted + or −5% the "margin step function". Each power supply module has a +5 V reference supplied by reference unit 80$_r$, which controls the output voltage of each power module, and any change in reference voltage causes a proportional change in output voltage.

The precision +5 V reference voltage has two programmable inputs for effecting +5% and −5% voltage change steps. The margin steps can be activated "locally" by a switch or "remotely" by the slave logic 90. Each logic power module has its own separate reference voltage and margin circuit.

The main AC power module (such as the 15 KW input module 41 of FIG. 15) can be set on or off via a TTL signal "S" from the power control circuit 80.

The cabinet control panel 44 (FIGS. 2, 15) enables "local mode" operation by a technician or system operator, and has an on/off push button with light-indicator, with power-failure/temperature-failure indicator and local/remote switch with indicator light.

Thus, the two modes for controlling power on/off are the "local" mode and the "remote" mode.

The local mode requires an "on-site" operator to manually start the power control on/off responses by use of an ON/OFF switch on cabinet control panel 44.

The remote mode allows the "system control" in the network whereby the master logic 100 (FIG. 8) instructs the appropriate slave logic 90 to command certain actions to its power control circuit 80.

The local/remote keyswitch in the cabinet control panel 44 enables or disables the local/remote interface (FIG. 16) in the power control circuit 80. Then depending on what mode the system is in, the sequencer 80$_q$ turns each power supply module on/off in the appropriate sequential order.

If a failure signal occurs on a power module, air sensor or temperature line (FIG. 16), then the sequencer 80$_q$ will power off the power modules in the appropriate sequence.

On "power-up" the proper sequence is to first turn on the main AC supply 41 after which power is turned on to the 2 V DC supply, then the 4.5 V and 5 V DC supply, and then the 12 V DC supply.

On "power-off", the sequence is effected in the reverse order.

As indicated in FIG. 15, each power module can furnish a TTL compatible "fail" signal to the sequencer 80$_p$ in the power control circuit 80.

The power sequencer 80$_q$ is a circuit which ensures that the main power module 41 is operating before checking the subordinate power modules, after which any incoming failure signal which is detected will make the sequencer shut off all the power modules in that subsystem. The sequencer 80$_q$ will also signal the slave logic 90 with a TTL compatible signal. Any failures are also indicated by light-emitting diodes which make reference to each power module. A similar failure indicator on the cabinet control panel 44 is also turned on.

Figures 17, 17A:
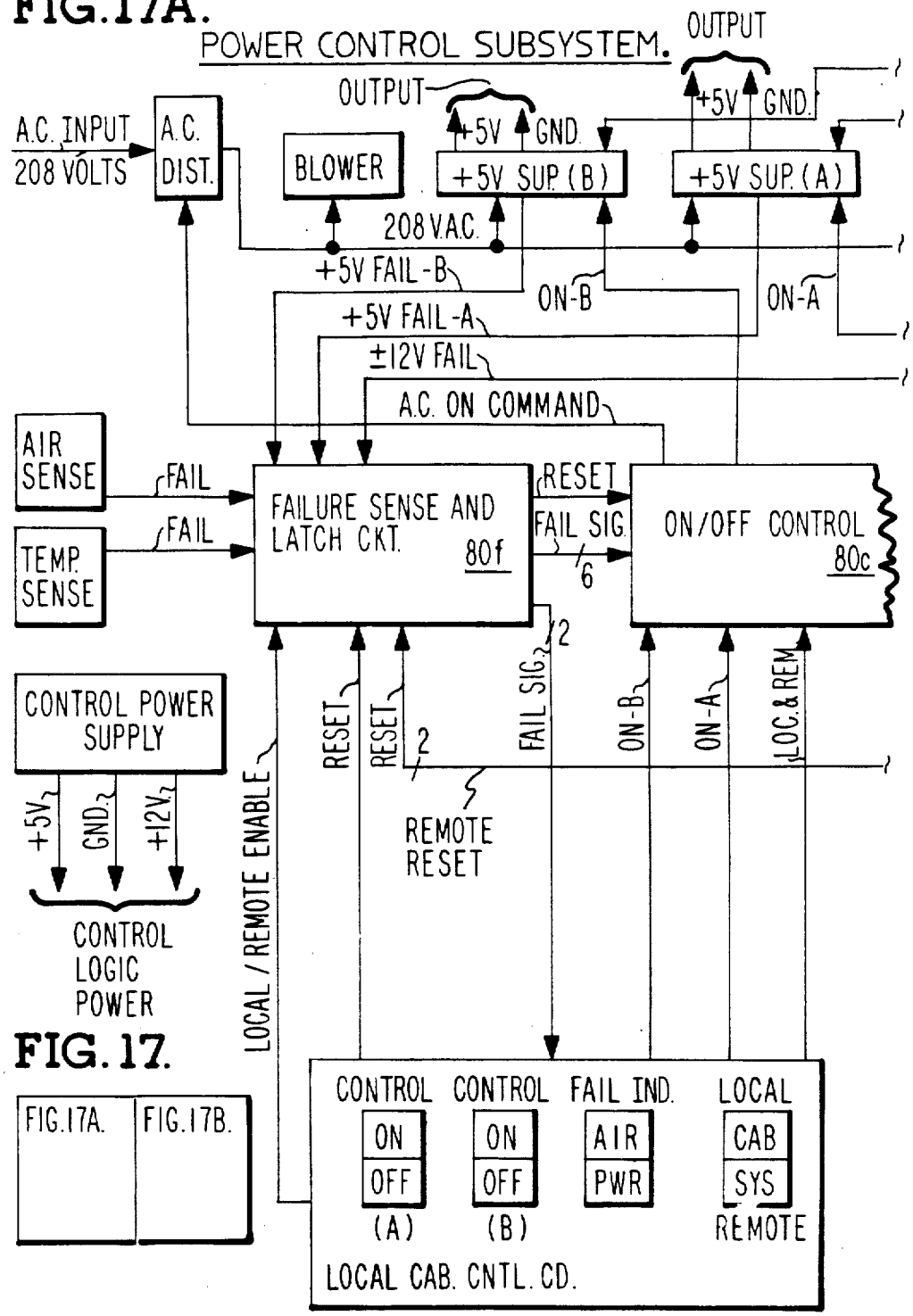
FIG. 17 is a block diagram of the local power switching control subsystem.
Figure 17B:
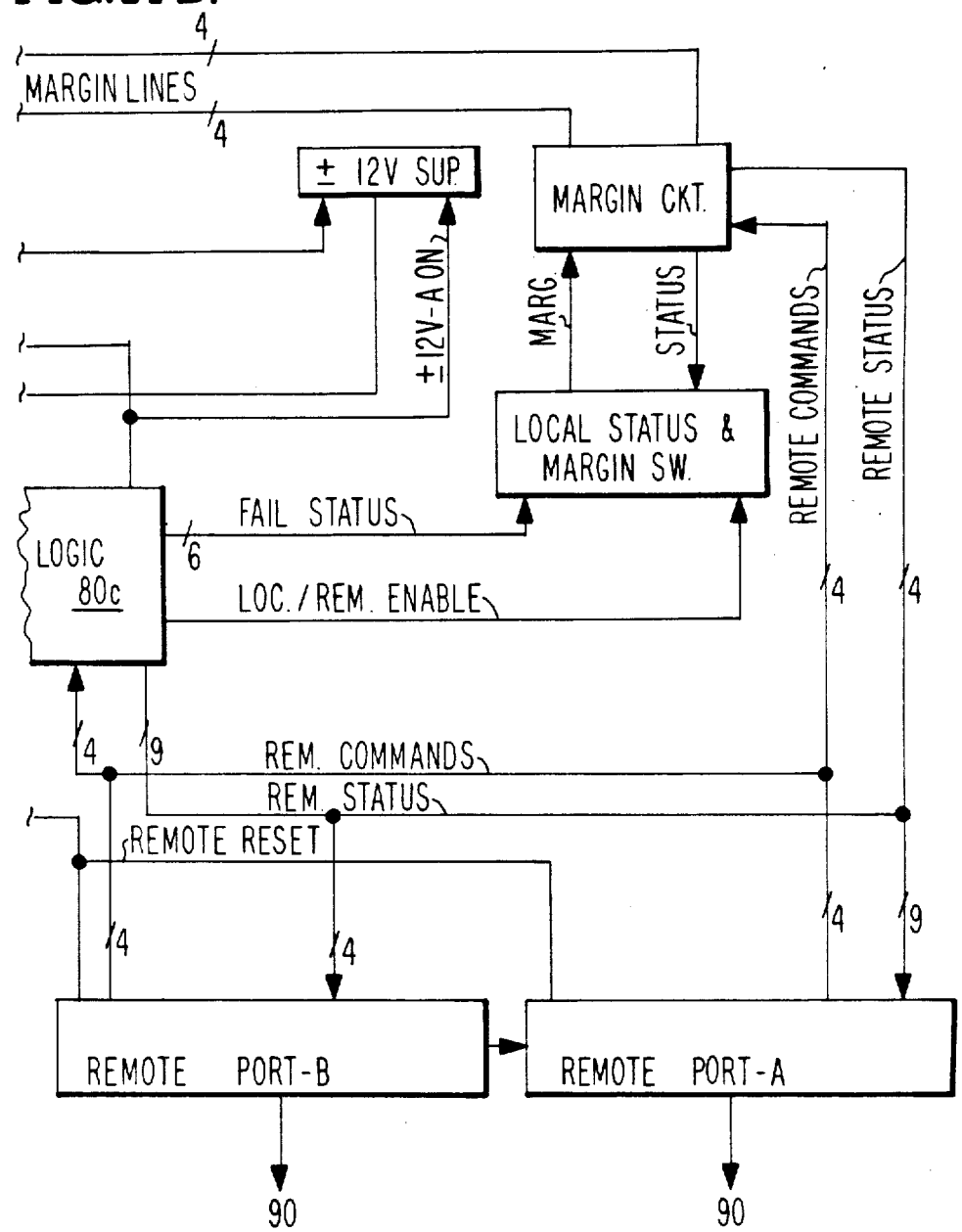

FIG. 17 shows an overall block of the local power control subsystem for each independently powered digital module.

The control logic unit 80$_c$ controls the power status of the main 208 volt AC power source which supplies power for the subordinate power modules of 5 volts and +/− 12 volts. The logic 80$_c$ further provides for the on/off sequencing of these subordinate power modules through a circuit such as seen in FIG. 18.

Figure 18:
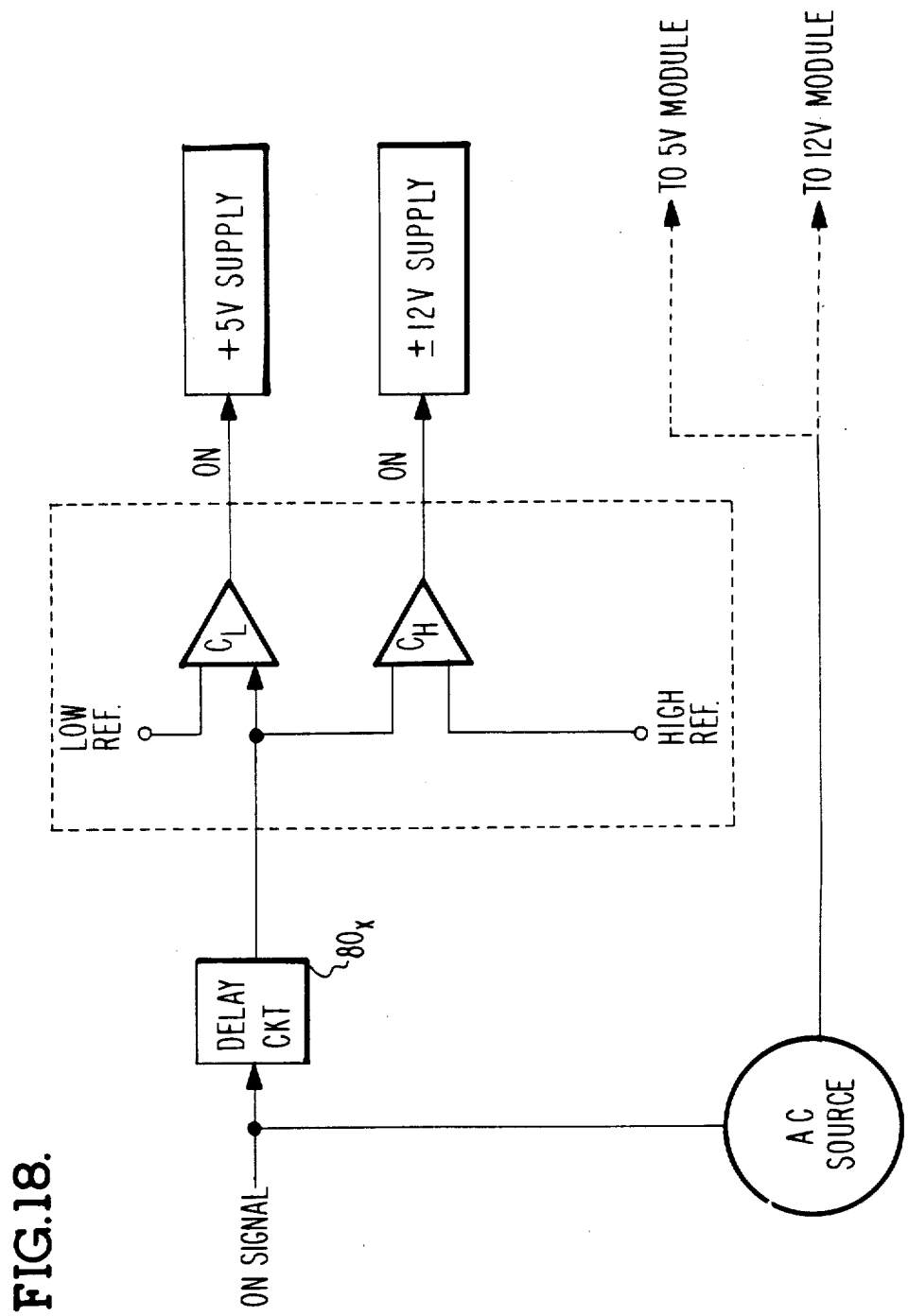
FIG. 18 is a schematic drawing illustrating the sequencing used for power up and power down of the subordinate power module units.

In FIG. 18, the ON signal will enable the AC power source to turn on. However, this power will not be applied to the 5 volt and 12 volt supplies until the ON signal operates to permit the main supply power to the subordinate supply. Here there is a first comparator $C_L$ set at a lower reference voltage and a second comparator set at a higher reference voltage. Thus, as the input voltage to each comparator "ramps up" in voltage, then the output of $C_L$ will "turn on" the 5 V supply. Then as the on signal increases in voltage it will later trip the $C_H$ comparator whose output will turn on the +/− 12 V supply. Thus, a "sequencing" effect powers up the lower voltage (5 V) subordinate supply before it can power up the higher voltage supply (+/− 12V).

On the "power down" cycle, the above circuitry will work in reverse sequence so that the 12 V supply will turn off before the 5 V supply is turned on.

The delay circuit 80$_X$ is used to delay the application of the "on" signal to the subordinate power supplies in order not to trigger the under-voltage sensing circuit during the turn-on cycle.

The power control subsystem described herein provides the ability to locally or remotely control the operation and report failure status of two independently controlled +5 volt power supplies and a +/− 12 volt power supply. Status can be read locally or remotely at any time but local or remote control commands must be enabled in order to function. Only one command source can be enabled at any time and must be selected at the local control panel by an alternative action LOCAL/REMOTE (CAB/SYS) switch.

Two independent ON/OFF control circuits are provided to turn on the +5 V−A and the +/− 12 volt supplies and the alternate +5V−B power supply. The sequence of events listed below takes place any time either supply is turned on, either locally or remotely.

1. A signal to the A.C. distribution module turns on the solid state relays to apply 208 volts A.C. to the blower and power supply inputs. A RESET is initiated at this time.
2. The RESET signal is sent to the FAILURE LATCH to clear any currently displayed failures if any. The RESET also triggers a UNDER VOLTAGE INHIBIT (UV INHIBIT) timer that disables the failure latch while the power supplies are turning on. This prevents any false failures indication while the power supply output voltage is ramping up to its nominal operating range.
3. There is a short delay after A.C. power is applied, then a signal is sent to the corresponding power supply to initiate the turn on cycle of the supply.
4. After the UV INHIBIT times out, any failure will be latched, and shut down the failed supply and not interrupt the other subsystem supplies. However, if the failure type is such that it would be detrimental to the entire power subsystem and logic cards, such as over temperature or blower failure, all supplies will be shut down and A.C. removed. The action that is taken by the ON/OFF control logic when a failure is determined by a programmable logic array (PAL) that is programmed for the desired results. All failure status is displayed so corrective action can be initiated.

There has herein been described a local power switching control subsystem which provides local power control, voltage adjustment and failure sensing (within the local module) for each powered digital module in a network. Each local power switching logic card further can receive instructions from a local slave logic unit and can also send status information to a master logic unit which may be situated within the local module or at a remote module.

While a preferred embodiment of the power switching control subsystem has been described, it should be understood that other possible embodiments may be devised within the framework of the following claims.

What is claimed is:

1. In a network connecting a plurality of digital modules where each digital module has its own local independent AC power source which is controllably supplied to a plurality of DC power modules also locally situated in each digital module, a local power control switching system in each of said digital modules comprising:
   a local primary source of AC power;
   a plurality of local DC power units energized by said AC power source under control of a local power control switching circuit means;
   said local power control switching circuit means including:
      means to control the connection or disconnection of said primary AC power source to each of said local DC power units;
      means to sequence the power-on connection or power-off disconnection to said local DC power units in a predetermined sequence;
      means to sense selected operating parameters in each of said digital modules and to generate a status signal for each parameter;
      operator switching means for enabling local power control from a local operator or a remote control unit.

2. The system of claim 1 wherein said local power control switching circuit means further includes:
   a local slave control-logic unit connected to said means to control the connection/disconnection;
   a remote master control-logic unit connected to said local slave-control logic unit, said master control-logic unit including:
      means to transmit power control commands to said local power control switching circuit means via said local slave control-logic unit when said operator switching means is switched to enable power control from said remote control unit.

3. The power control switching system of claim 1, wherein each of said DC power units include:
   means for transmitting status data to said local power control switching circuit means to indicate a condition of over-voltage, under-voltage, over-current or over-temperature.

4. The power control switching system of claim 1, which includes:
   means for selecting a local mode operation or remote mode operation;
   manual switch means in said local power control switching circuit means for setting the power status of each of said DC power supply units when local mode is selected;
   remote interface means for reading out to said remote unit the power status of each of said DC power units when said remote mode is selected.

5. The control system of claim 4, wherein said power control switching means includes:
   means for transmitting power status information data to said remote unit when said remote mode is selected.

6. The control system of claim 1, wherein said sequence means includes hardwired circuitry to execute a power up sequence which first turns on said local primary AC source power and then sequentially turns on a series of said DC power units starting with the lowest voltage DC power unit and progressing next to the next-higher voltage DC power unit until each of said DC power supply units are powered up.

7. The control system of claim 6, wherein said sequence means includes hardwired circuitry to execute a power down sequence of operations by shutting off the highest voltage DC power unit and progressing sequentially to the next lower DC voltage power unit until each of said DC power units are shut off.

8. A plurality of digital modules connected in a network for power control operations, each of which modules has its own primary source of local AC power for supplying a local plurality of DC power units located therein, a power control system comprising:
   a plurality of local power control switching and sequencing logic units, each of said logic units located within said local digital module and including:
      means for controlling each of the said primary AC power sources for connecting/disconnecting power to each of said local DC power units;
      hardware means for sequencing the turn on or turn off of AC power to each of said DC power units in a predetermined sequence;
      means for receiving power control switching commands from either a local cabinet operator switch means or from a remote control unit means;
      hardware checking means for sensing voltage temperature and air flow parameters so as to shut down said primary AC power when said voltage, temperature and air flow parameters are beyond a prescribed tolerance;
      said local cabinet operator switch means providing manual setting for power on/off of said AC and DC power units;
      said remote control unit means for transmitting power on/off commands to each of said local power control and sequencing means when said means for receiving is set for remote control unit operation.

9. The system of claim 8 wherein said hardware means for sequencing operates to empower lower voltage output DC power units before empowering higher voltage output DC power units.

10. The system of claim 8 wherein each of said local cabinet operator switch means includes:

means for increasing/decreasing voltage output of each of said DC power units in fixed percentage steps.

11. The system of claim 10 wherein each said local cabinet operator switch means includes:
means for placing said local digital module AC and DC power units under operative control at said remote control means.

12. The system of claim 8 wherein upon failure of said remote control means, the power control for each local digital module will revert to that set by said local cabinet operator switch means.

13. The system of claim 8 wherein upon failure of said remote control means, said local digital module will empower a panel light to indicate to the local operator that said local cabinet operator switch means should be controlled by said local operator.

14. A local power control system controlling power for a local digital module in which module power may also be controlled from a remote control unit which remote unit is also connected to control the power of other digital modules in a network, the combination comprising;

a plurality of independent primary sources of AC power, each AC power source situated locally for each digital module and where each AC source is connected to a plurality of local DC power units located in each said local digital modules and each local AC and local DC power units operate under control of a local power control switching unit;

said plurality of local DC power units connected to said local power control switching unit for switching on or off said DC units in a predetermined sequence;

said local power control switching unit including:
selection means to receive power-command information via local operator control or from said remote control unit;
means to operate on preset local operator command control upon failure of or disconnection from said remote control unit;
means to switch power on/off of said DC units in a predetermined sequence via internal hardwared circuitry upon command from said local control or remote control unit.

* * * * *